US009084618B2

(12) United States Patent
Serbousek et al.

(10) Patent No.: US 9,084,618 B2
(45) Date of Patent: Jul. 21, 2015

(54) DRILL GUIDES FOR CONFIRMING ALIGNMENT OF PATIENT-SPECIFIC ALIGNMENT GUIDES

(75) Inventors: Jon C. Serbousek, Winona Lake, IN (US); Todd O. Davis, Leesburg, IN (US); Joshua B. Catanzarite, Warsaw, IN (US); Brian A. Uthgenannt, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 203 days.

(21) Appl. No.: 13/493,509

(22) Filed: Jun. 11, 2012

(65) Prior Publication Data

US 2012/0316564 A1 Dec. 13, 2012

Related U.S. Application Data

(60) Provisional application No. 61/496,085, filed on Jun. 13, 2011.

(51) Int. Cl.

*A61B 17/58* (2006.01)
*A61B 17/60* (2006.01)
*A61F 2/00* (2006.01)

(Continued)

(52) U.S. Cl.

CPC ........... *A61B 17/1764* (2013.01); *A61B 17/155* (2013.01); *A61B 2017/568* (2013.01)

(58) Field of Classification Search

USPC ........................................ 606/87–89, 96, 102

See application file for complete search history.

(56) References Cited

U.S. PATENT DOCUMENTS 1,480,285 A 1/1924 Moore
2,181,746 A 11/1939 Siebrandt (Continued)

FOREIGN PATENT DOCUMENTS

CA 2447694 A1 12/2002
CA 2501041 A1 4/2004

(Continued)

OTHER PUBLICATIONS

International Search Report and Written Opinion for PCT/US2013/026875 mailed Jun. 7, 2013, claiming benefit of U.S. Appl. No. 13/400,652, filed Feb. 21, 2012.

(Continued)

*Primary Examiner* — Andrew Yang
*Assistant Examiner* — Olivia C Chang
(74) *Attorney, Agent, or Firm* — Harness, Dickey

(57) ABSTRACT

An orthopedic device includes a drill guide configured to be mounted on a patient-specific alignment guide for intraoperatively confirming alignment of the patient-specific alignment guide relative to a bone. The patient-specific alignment guide includes first and second referencing holes. The drill guide includes a main body with a first coupling member and a second coupling member. The first and second coupling members are configured to be received within the first and second referencing holes, respectively. The first and second coupling members each include corresponding first and second drill openings configured to align with the first and second referencing holes, respectively. The drill openings each guide a drilling tool toward the bone to drill corresponding holes in the bone. The main body also includes an alignment confirmation feature configured for confirming alignment of the patient-specific alignment guide relative to the bone before drilling holes in the bone.

22 Claims, 7 Drawing Sheets

(51) Int. Cl.

| | |
|---|---|
| ***A61B 17/17*** | (2006.01) |
| *A61B 17/15* | (2006.01) |
| *A61B 17/56* | (2006.01) |

(56) References Cited

U.S. PATENT DOCUMENTS 2,407,845 A 9/1946 Nemeyer et al.
2,416,228 A 2/1947 Sheppard
2,618,913 A 11/1952 Plancon et al.
2,910,978 A 11/1959 Urist
3,330,611 A 7/1967 Heifetz
3,840,904 A 10/1974 Tronzo
3,975,858 A 8/1976 Much
4,246,895 A 1/1981 Rehder
4,306,866 A 12/1981 Weissman
4,324,006 A 4/1982 Charnley
4,421,112 A 12/1983 Mains et al.
4,436,684 A 3/1984 White
4,457,306 A 7/1984 Borzone
4,475,549 A 10/1984 Oh
4,506,393 A 3/1985 Murphy
4,524,766 A 6/1985 Petersen
4,528,980 A 7/1985 Kenna
4,565,191 A 1/1986 Slocum
4,619,658 A 10/1986 Pappas et al.
4,621,630 A 11/1986 Kenna
4,632,111 A 12/1986 Roche
4,633,862 A 1/1987 Petersen
4,663,720 A 5/1987 Duret et al.
4,689,984 A 9/1987 Kellner
4,695,283 A 9/1987 Aldinger
4,696,292 A 9/1987 Heiple
4,703,751 A 11/1987 Pohl
4,704,686 A 11/1987 Aldinger
4,706,660 A 11/1987 Petersen
4,719,907 A 1/1988 Banko et al.
4,721,104 A 1/1988 Kaufman et al.
4,722,330 A 2/1988 Russell et al.
4,759,350 A 7/1988 Dunn et al.
4,778,474 A 10/1988 Homsy
4,800,874 A 1/1989 David et al.
4,821,213 A 4/1989 Cline et al.
4,822,365 A 4/1989 Walker et al.
4,841,975 A 6/1989 Woolson
4,846,161 A 7/1989 Roger
4,871,975 A 10/1989 Nawata et al.
4,892,545 A 1/1990 Day et al.
4,893,619 A 1/1990 Dale et al.
4,896,663 A 1/1990 Vandewalls
4,907,577 A 3/1990 Wu
4,927,422 A 5/1990 Engelhardt
4,936,862 A 6/1990 Walker et al.
4,952,213 A 8/1990 Bowman et al.
4,959,066 A 9/1990 Dunn et al.
4,976,737 A 12/1990 Leake
4,979,949 A 12/1990 Matsen, III et al.
4,985,037 A 1/1991 Petersen
5,002,579 A 3/1991 Copf et al.
5,006,121 A 4/1991 Hafeli
5,007,936 A 4/1991 Woolson
5,030,219 A 7/1991 Matsen, III et al.
5,030,221 A 7/1991 Buechel et al.
5,041,117 A 8/1991 Engelhardt
5,053,037 A 10/1991 Lackey
5,053,039 A 10/1991 Hofmann et al.
5,056,351 A 10/1991 Stiver et al.
5,086,401 A 2/1992 Glassman et al.
5,098,383 A 3/1992 Hemmy et al.
5,098,436 A 3/1992 Ferrante et al.
5,108,425 A 4/1992 Hwang
5,122,144 A 6/1992 Bert et al.
5,123,927 A 6/1992 Duncan et al.
5,129,908 A 7/1992 Petersen
5,129,909 A 7/1992 Sutherland
5,133,760 A 7/1992 Petersen et al.
5,140,777 A 8/1992 Ushiyama et al.
5,150,304 A 9/1992 Berchem et al.
5,176,684 A 1/1993 Ferrante et al.
5,194,066 A 3/1993 Van Zile
5,234,433 A 8/1993 Bert et al.
5,246,444 A 9/1993 Schreiber
5,253,506 A 10/1993 Davis et al.
5,258,032 A 11/1993 Bertin
5,261,915 A 11/1993 Durlacher et al.
5,274,565 A 12/1993 Reuben
5,282,802 A 2/1994 Mahony, III
5,299,288 A 3/1994 Glassman et al.
5,300,077 A 4/1994 Howell
5,320,529 A 6/1994 Pompa
5,320,625 A 6/1994 Bertin
5,323,697 A 6/1994 Schrock
5,342,366 A 8/1994 Whiteside et al.
5,344,423 A 9/1994 Dietz et al.
5,360,446 A 11/1994 Kennedy
5,364,402 A 11/1994 Mumme et al.
5,368,858 A 11/1994 Hunziker
5,370,692 A 12/1994 Fink et al.
5,370,699 A 12/1994 Hood et al.
5,405,395 A 4/1995 Coates
5,408,409 A 4/1995 Glassman et al.
5,411,521 A 5/1995 Putnam et al.
5,415,662 A 5/1995 Ferrante et al.
5,417,694 A 5/1995 Marik et al.
5,438,263 A 8/1995 Dworkin et al.
5,440,496 A 8/1995 Andersson et al.
5,448,489 A 9/1995 Reuben
5,449,360 A 9/1995 Schreiber
5,452,407 A 9/1995 Crook
5,454,816 A 10/1995 Ashby
5,462,550 A 10/1995 Dietz et al.
5,472,415 A 12/1995 King et al.
5,474,559 A 12/1995 Bertin et al.
5,490,854 A 2/1996 Fisher et al.
5,496,324 A 3/1996 Barnes
5,507,833 A 4/1996 Bohn
5,514,519 A 5/1996 Neckers
5,520,695 A 5/1996 Luckman
5,527,317 A 6/1996 Ashby et al.
5,539,649 A 7/1996 Walsh et al.
5,540,695 A 7/1996 Levy
5,545,222 A 8/1996 Bonutti
5,549,688 A 8/1996 Ries et al.
5,554,190 A 9/1996 Draenert
5,560,096 A 10/1996 Stephens
5,571,110 A 11/1996 Matsen, III et al.
5,578,037 A 11/1996 Sanders et al.
5,593,411 A 1/1997 Stalcup et al.
5,595,703 A 1/1997 Swaelens et al.
5,601,565 A 2/1997 Huebner
5,607,431 A 3/1997 Dudasik et al.
5,611,802 A 3/1997 Samuelson et al.
5,613,969 A 3/1997 Jenkins, Jr.
5,620,448 A 4/1997 Puddu
5,634,927 A 6/1997 Houston et al.
5,641,323 A 6/1997 Caldarise
5,653,714 A 8/1997 Dietz et al.
5,658,294 A 8/1997 Sederholm
5,662,656 A 9/1997 White
5,662,710 A 9/1997 Bonutti
5,671,018 A 9/1997 Ohara et al.
5,676,668 A 10/1997 McCue et al.
5,677,107 A 10/1997 Neckers
5,681,354 A 10/1997 Eckhoff
5,682,886 A 11/1997 Delp et al.
5,683,469 A 11/1997 Johnson et al.
5,690,635 A 11/1997 Matsen, III et al.
5,697,933 A 12/1997 Gundlapalli et al.
5,702,460 A 12/1997 Carls et al.
5,702,464 A 12/1997 Lackey et al.
5,704,941 A 1/1998 Jacober et al.
5,709,689 A 1/1998 Ferrante et al.
5,720,752 A 2/1998 Elliott et al.
5,722,978 A 3/1998 Jenkins, Jr.
5,725,376 A 3/1998 Poirier

(56) References Cited

U.S. PATENT DOCUMENTS 5,725,593 A 3/1998 Caracciolo
5,735,277 A 4/1998 Schuster
5,745,834 A 4/1998 Bampton et al.
5,748,767 A 5/1998 Raab
5,749,875 A 5/1998 Puddu
5,749,876 A 5/1998 Duvillier et al.
5,762,125 A 6/1998 Mastrorio
5,766,251 A 6/1998 Koshino et al.
5,768,134 A 6/1998 Swaelens et al.
5,769,092 A 6/1998 Williamson, Jr.
5,776,200 A 7/1998 Johnson et al.
5,786,217 A 7/1998 Tubo et al.
5,792,143 A 8/1998 Samuelson et al.
5,798,924 A 8/1998 Eufinger et al.
5,799,055 A 8/1998 Peshkin et al.
5,835,619 A 11/1998 Morimoto et al.
5,860,980 A 1/1999 Axelson, Jr. et al.
5,860,981 A 1/1999 Bertin et al.
5,871,018 A 2/1999 Delp et al.
5,876,456 A 3/1999 Sederholm et al.
5,879,398 A 3/1999 Swarts et al.
5,879,402 A 3/1999 Lawes et al.
5,880,976 A 3/1999 DiGioia, III et al.
5,885,297 A 3/1999 Matsen, III
5,885,298 A 3/1999 Herrington et al.
5,888,219 A 3/1999 Bonutti
5,895,389 A 4/1999 Schenk et al.
5,899,907 A 5/1999 Johnson
5,901,060 A 5/1999 Schall et al.
5,911,724 A 6/1999 Wehrli
5,921,988 A 7/1999 Legrand
5,925,049 A 7/1999 Gustilo et al.
5,942,370 A 8/1999 Neckers
5,967,777 A 10/1999 Klein et al.
5,976,149 A 11/1999 Masini
5,980,526 A 11/1999 Johnson et al.
6,008,433 A 12/1999 Stone
6,019,767 A 2/2000 Howell
6,033,415 A 3/2000 Mittelstadt et al.
6,042,612 A 3/2000 Voydeville
6,056,754 A 5/2000 Haines et al.
6,059,789 A 5/2000 Dinger et al.
6,059,833 A 5/2000 Doets
6,066,175 A 5/2000 Henderson et al.
6,086,593 A 7/2000 Bonutti
6,120,510 A 9/2000 Albrektsson et al.
6,120,544 A 9/2000 Grundei et al.
6,126,690 A 10/2000 Ateshian et al.
6,126,692 A 10/2000 Robie et al.
6,136,033 A 10/2000 Suemer
6,156,069 A 12/2000 Amstutz
6,159,217 A 12/2000 Robie et al.
6,161,080 A 12/2000 Aouni-Ateshian et al.
6,162,257 A 12/2000 Gustilo et al.
6,187,010 B1 2/2001 Masini
6,195,615 B1 2/2001 Lysen
6,203,546 B1 3/2001 MacMahon
6,205,411 B1 3/2001 DiGioia, III et al.
6,206,927 B1 3/2001 Fell et al.
6,210,445 B1 4/2001 Zawadzki
6,238,435 B1 5/2001 Meulink et al.
6,254,604 B1 7/2001 Howell
6,258,097 B1 7/2001 Cook et al.
6,264,698 B1 7/2001 Lawes et al.
6,270,529 B1 8/2001 Terrill-Grisoni et al.
6,273,891 B1 8/2001 Masini
6,290,727 B1 9/2001 Otto et al.
6,293,971 B1 9/2001 Nelson et al.
6,302,913 B1 10/2001 Ripamonti et al.
6,310,269 B1 10/2001 Friese et al.
6,312,258 B1 11/2001 Ashman
6,312,473 B1 11/2001 Oshida
6,319,285 B1 11/2001 Chamier et al.
6,322,728 B1 11/2001 Brodkin et al.
6,325,829 B1 12/2001 Schmotzer
6,327,491 B1 12/2001 Franklin et al.
6,338,738 B1 1/2002 Bellotti et al.
6,343,987 B2 2/2002 Hayama et al.
6,354,011 B1 3/2002 Albrecht
6,361,563 B2 3/2002 Terrill-Grisoni et al.
6,379,299 B1 4/2002 Borodulin et al.
6,379,388 B1 4/2002 Ensign et al.
6,383,228 B1 5/2002 Schmotzer
6,391,251 B1 5/2002 Keicher et al.
6,395,005 B1 5/2002 Lovell
6,424,332 B1 7/2002 Powell
6,427,698 B1 8/2002 Yoon
6,459,948 B1 10/2002 Ateshian et al.
6,463,351 B1 10/2002 Clynch
6,475,243 B1 11/2002 Sheldon et al.
6,482,236 B2 11/2002 Habecker
6,488,715 B1 12/2002 Pope et al.
6,503,255 B1 1/2003 Albrektsson et al.
6,508,980 B1 1/2003 Sachs et al.
6,510,334 B1 1/2003 Schuster et al.
6,514,259 B2 2/2003 Picard et al.
6,517,583 B1 2/2003 Pope et al.
6,519,998 B2 2/2003 Ertl et al.
6,520,964 B2 2/2003 Tallarida et al.
6,533,737 B1 3/2003 Brosseau et al.
6,547,823 B2 4/2003 Scarborough et al.
6,551,325 B2 4/2003 Neubauer et al.
6,554,837 B1 4/2003 Hauri et al.
6,556,008 B2 4/2003 Thesen
6,558,391 B2 5/2003 Axelson, Jr. et al.
6,558,428 B2 5/2003 Park
6,562,073 B2 5/2003 Foley
6,564,085 B2 5/2003 Meaney et al.
6,567,681 B1 5/2003 Lindequist
6,575,980 B1 6/2003 Robie et al.
6,575,982 B1 6/2003 Bonutti
6,591,581 B2 7/2003 Schmieding
6,605,293 B1 8/2003 Giordano et al.
6,610,067 B2 8/2003 Tallarida et al.
6,622,567 B1 9/2003 Hamel et al.
6,629,999 B1 10/2003 Serafin, Jr.
6,641,617 B1 11/2003 Merrill et al.
6,676,892 B2 1/2004 Das et al.
6,682,566 B2 1/2004 Draenert
6,696,073 B2 2/2004 Boyce et al.
6,697,664 B2 2/2004 Kienzle, III et al.
6,701,174 B1 3/2004 Krause et al.
6,709,462 B2 3/2004 Hanssen
6,711,431 B2 3/2004 Sarin et al.
6,711,432 B1 3/2004 Krause et al.
6,712,856 B1 3/2004 Carignan et al.
6,716,249 B2 4/2004 Hyde
6,725,077 B1 4/2004 Balloni et al.
6,738,657 B1 5/2004 Franklin et al.
6,740,092 B2 5/2004 Lombardo et al.
6,749,638 B1 6/2004 Saladino
6,750,653 B1 6/2004 Zou et al.
6,772,026 B2 8/2004 Bradbury et al.
6,780,190 B2 8/2004 Maroney
6,786,930 B2 9/2004 Biscup
6,799,066 B2 9/2004 Steines et al.
6,823,871 B2 11/2004 Schmieding
6,827,723 B2 12/2004 Carson
6,887,247 B1 5/2005 Couture et al.
6,905,514 B2 6/2005 Carignan et al.
6,916,324 B2 7/2005 Sanford et al.
6,923,817 B2 8/2005 Carson et al.
6,923,831 B2 8/2005 Fell et al.
6,932,842 B1 8/2005 Litschko et al.
6,942,475 B2 9/2005 Ensign et al.
6,944,518 B2 9/2005 Roose
6,945,976 B2 9/2005 Ball et al.
6,953,480 B2 10/2005 Mears et al.
6,960,216 B2 11/2005 Kolb et al.
6,975,755 B1 12/2005 Baumberg
6,990,220 B2 1/2006 Ellis et al.
6,993,406 B1 1/2006 Cesarano, III et al.
7,001,385 B2 2/2006 Bonutti
7,029,479 B2 4/2006 Tallarida et al.

(56) References Cited

U.S. PATENT DOCUMENTS 7,042,222 B2 5/2006 Zheng et al.
7,048,741 B2 5/2006 Swanson
7,050,877 B2 5/2006 Iseki et al.
7,060,074 B2 6/2006 Rosa et al.
7,074,241 B2 7/2006 McKinnon
RE39,301 E 9/2006 Bertin
7,104,997 B2 9/2006 Lionberger et al.
7,105,026 B2 9/2006 Johnson et al.
7,115,131 B2 10/2006 Engh et al.
7,121,832 B2 10/2006 Hsieh et al.
7,141,053 B2 11/2006 Rosa et al.
D533,664 S 12/2006 Buttler et al.
7,169,185 B2 1/2007 Sidebotham
7,174,282 B2 2/2007 Hollister et al.
7,176,466 B2 2/2007 Rousso et al.
7,184,814 B2 2/2007 Lang et al.
7,198,628 B2 4/2007 Ondrla et al.
7,218,232 B2 5/2007 DiSilvestro et al.
7,239,908 B1 7/2007 Alexander et al.
7,241,315 B2 7/2007 Evans
7,255,702 B2 8/2007 Serra et al.
7,258,701 B2 8/2007 Aram et al.
7,275,218 B2 9/2007 Petrella et al.
7,282,054 B2 10/2007 Steffensmeier et al.
7,294,133 B2 11/2007 Zink et al.
7,297,164 B2 11/2007 Johnson et al.
7,309,339 B2 12/2007 Cusick et al.
7,333,013 B2 2/2008 Berger
7,335,231 B2 2/2008 McLean
7,371,260 B2 5/2008 Malinin
7,383,164 B2 6/2008 Aram et al.
7,385,498 B2 6/2008 Dobosz
7,388,972 B2 6/2008 Kitson
7,390,327 B2 6/2008 Collazo et al.
7,392,076 B2 6/2008 Moctezuma de La Barrera
7,427,200 B2 9/2008 Noble et al.
7,427,272 B2 9/2008 Richard et al.
7,468,075 B2 12/2008 Lang et al.
7,474,223 B2 1/2009 Nycz et al.
7,488,325 B2 2/2009 Qian
7,494,510 B2 2/2009 Zweymuller
7,517,365 B2 4/2009 Carignan et al.
7,527,631 B2 5/2009 Maroney et al.
7,534,263 B2 5/2009 Burdulis, Jr. et al.
7,537,664 B2 5/2009 O'Neill et al.
7,542,791 B2 6/2009 Mire et al.
7,559,931 B2 7/2009 Stone
7,575,602 B2 8/2009 Amirouche et al.
7,578,851 B2 8/2009 Dong et al.
7,582,091 B2 9/2009 Duncan et al.
7,591,821 B2 9/2009 Kelman
7,601,155 B2 10/2009 Petersen
7,603,192 B2 10/2009 Martin et al.
7,604,639 B2 10/2009 Swanson
7,611,516 B2 11/2009 Maroney
7,618,451 B2 11/2009 Berez et al.
7,621,915 B2 11/2009 Frederick et al.
7,625,409 B2 12/2009 Saltzman et al.
7,646,161 B2 1/2010 Albu-Schaffer et al.
7,651,501 B2 1/2010 Penenberg et al.
7,670,345 B2 3/2010 Plassky et al.
7,682,398 B2 3/2010 Croxton et al.
7,695,477 B2 4/2010 Creger et al.
7,695,521 B2 4/2010 Ely et al.
7,699,847 B2 4/2010 Sheldon et al.
7,704,253 B2 4/2010 Bastian et al.
7,723,395 B2 5/2010 Ringeisen et al.
7,747,305 B2 6/2010 Dean et al.
D622,854 S 8/2010 Otto et al.
7,780,672 B2 8/2010 Metzger et al.
7,780,740 B2 8/2010 Steinberg
7,789,885 B2 9/2010 Metzger
7,794,466 B2 9/2010 Merchant et al.
7,794,467 B2 9/2010 McGinley et al.
7,794,504 B2 9/2010 Case
7,806,896 B1 10/2010 Bonutti
7,809,184 B2 10/2010 Neubauer et al.
7,819,925 B2 10/2010 King et al.
7,828,806 B2 11/2010 Graf et al.
7,833,245 B2 11/2010 Kaes et al.
7,837,690 B2 11/2010 Metzger
7,850,698 B2 12/2010 Straszheim-Morley et al.
7,879,109 B2 2/2011 Borden et al.
7,892,261 B2 2/2011 Bonutti
7,896,921 B2 3/2011 Smith et al.
7,926,363 B2 4/2011 Miller et al.
7,935,119 B2 5/2011 Ammann et al.
7,935,150 B2 5/2011 Carignan et al.
7,938,861 B2 5/2011 King et al.
7,959,637 B2 6/2011 Fox et al.
7,962,196 B2 6/2011 Tuma
7,963,968 B2 6/2011 Dees, Jr.
7,967,823 B2 6/2011 Ammann et al.
7,967,868 B2 6/2011 White et al.
7,974,677 B2 7/2011 Mire et al.
7,981,158 B2 7/2011 Fitz et al.
7,988,736 B2 8/2011 May et al.
7,993,353 B2 8/2011 Rossner et al.
8,062,301 B2 11/2011 Ammann et al.
8,066,708 B2 11/2011 Lang et al.
8,070,752 B2 12/2011 Metzger et al.
8,083,745 B2 12/2011 Lang et al.
8,083,746 B2 12/2011 Novak
8,083,749 B2 12/2011 Taber
8,086,336 B2 12/2011 Christensen
8,092,465 B2 1/2012 Metzger et al.
8,105,330 B2 1/2012 Fitz et al.
8,122,582 B2 2/2012 Burdulis, Jr. et al.
8,133,230 B2 3/2012 Stevens et al.
8,133,234 B2 3/2012 Meridew et al.
8,137,406 B2 3/2012 Novak et al.
8,147,861 B2 4/2012 Jones et al.
8,160,345 B2 4/2012 Pavlovskaia et al.
8,167,951 B2 5/2012 Ammann et al.
8,170,641 B2 5/2012 Belcher
8,182,489 B2 5/2012 Horacek
8,192,441 B2 6/2012 Collazo
8,192,495 B2 6/2012 Simpson et al.
8,200,355 B2 6/2012 Lee et al.
8,211,112 B2 7/2012 Novak et al.
8,221,430 B2 7/2012 Park et al.
8,241,292 B2 8/2012 Collazo
8,241,293 B2 8/2012 Stone et al.
8,246,680 B2 8/2012 Betz et al.
8,260,589 B1 9/2012 Kumar
8,265,790 B2 9/2012 Amiot et al.
8,268,099 B2 9/2012 O'Neill et al.
8,268,100 B2 9/2012 O'Neill et al.
D669,176 S 10/2012 Frey
8,282,646 B2 10/2012 Schoenefeld et al.
8,298,237 B2 10/2012 Schoenefeld et al.
8,303,596 B2 11/2012 Plaβky et al.
8,313,491 B2 11/2012 Green, II et al.
D672,038 S 12/2012 Frey
8,333,772 B2 12/2012 Fox et al.
8,337,503 B2 12/2012 Lian
8,355,773 B2 1/2013 Leitner et al.
8,372,078 B2 2/2013 Collazo
8,377,066 B2 2/2013 Katrana et al.
8,388,690 B2 3/2013 Singhatat et al.
8,398,646 B2 3/2013 Metzger et al.
8,407,067 B2 3/2013 Uthgenannt et al.
8,414,594 B2 4/2013 Berger et al.
8,419,741 B2 4/2013 Carignan et al.
8,425,522 B2 4/2013 Bonutti
8,430,882 B2 4/2013 Lowry et al.
8,430,931 B2 4/2013 Acker et al.
8,439,675 B2 5/2013 De Moyer
8,439,925 B2 5/2013 Marino et al.
8,444,564 B2 5/2013 Mahfouz et al.
8,444,651 B2 5/2013 Kunz et al.
8,457,930 B2 6/2013 Schroeder
8,460,302 B2 6/2013 Park et al.
8,469,961 B2 6/2013 Alleyne et al.

(56) References Cited

U.S. PATENT DOCUMENTS 8,473,305 B2 6/2013 Belcher et al.
8,486,150 B2 7/2013 White et al.
8,500,740 B2 8/2013 Bojarski et al.
8,532,361 B2 9/2013 Pavlovskaia et al.
8,532,806 B1 9/2013 Masson
8,532,807 B2 9/2013 Metzger
8,535,387 B2 9/2013 Meridew et al.
8,543,234 B2 9/2013 Gao
8,545,508 B2 10/2013 Collazo
8,568,487 B2 10/2013 Witt et al.
8,591,516 B2 11/2013 Metzger et al.
8,597,365 B2 12/2013 Meridew
8,603,180 B2 12/2013 White et al.
8,608,748 B2 12/2013 Metzger et al.
8,608,749 B2 12/2013 Meridew et al.
8,617,170 B2 12/2013 Ashby et al.
8,617,174 B2 12/2013 Axelson, Jr. et al.
8,617,175 B2 12/2013 Park et al.
8,632,547 B2 1/2014 Maxson et al.
8,652,142 B2 2/2014 Geissler
8,668,700 B2 3/2014 Catanzarite et al.
8,702,712 B2 4/2014 Jordan et al.
8,702,715 B2 4/2014 Ammann et al.
8,715,289 B2 5/2014 Smith
8,764,760 B2 7/2014 Metzger et al.
8,777,875 B2 7/2014 Park
8,828,016 B2 9/2014 Major et al.
8,828,087 B2 9/2014 Stone et al.
8,828,089 B1 9/2014 Perez et al.
8,834,568 B2 9/2014 Shapiro
8,956,364 B2 2/2015 Catanzarite et al.
8,979,936 B2 3/2015 White et al.
9,005,297 B2 4/2015 Katrana et al.
2001/0005797 A1 6/2001 Barlow et al.
2001/0011190 A1 8/2001 Park
2001/0021876 A1 9/2001 Terrill-Grisoni et al.
2001/0054478 A1 12/2001 Watanabe et al.
2002/0007294 A1 1/2002 Bradbury et al.
2002/0029045 A1 3/2002 Bonutti
2002/0052606 A1 5/2002 Bonutti
2002/0059049 A1 5/2002 Bradbury et al.
2002/0082741 A1 6/2002 Mazumder et al.
2002/0087274 A1 7/2002 Alexander et al.
2002/0092532 A1 7/2002 Yoon
2002/0107522 A1 8/2002 Picard et al.
2002/0128872 A1 9/2002 Giammattei
2002/0147415 A1 10/2002 Martelli
2002/0186818 A1 12/2002 Arnaud et al.
2002/0193797 A1 12/2002 Johnson et al.
2002/0198528 A1 12/2002 Engh et al.
2002/0198531 A1 12/2002 Millard et al.
2003/0009171 A1 1/2003 Tornier
2003/0009234 A1 1/2003 Treacy et al.
2003/0011624 A1 1/2003 Ellis
2003/0018338 A1 1/2003 Axelson et al.
2003/0039676 A1 2/2003 Boyce et al.
2003/0055502 A1 3/2003 Lang et al.
2003/0105526 A1 6/2003 Bryant et al.
2003/0109784 A1 6/2003 Loh et al.
2003/0120276 A1 6/2003 Tallarida et al.
2003/0130741 A1 7/2003 McMinn
2003/0139817 A1 7/2003 Tuke et al.
2003/0158606 A1 8/2003 Coon et al.
2003/0171757 A1 9/2003 Coon et al.
2003/0216669 A1 11/2003 Lang et al.
2004/0018144 A1 1/2004 Briscoe
2004/0030245 A1 2/2004 Noble et al.
2004/0054372 A1 3/2004 Corden et al.
2004/0054416 A1 3/2004 Wyss et al.
2004/0068187 A1 4/2004 Krause et al.
2004/0092932 A1 5/2004 Aubin et al.
2004/0098133 A1 5/2004 Carignan et al.
2004/0102852 A1 5/2004 Johnson et al.
2004/0102866 A1 5/2004 Harris et al.
2004/0106926 A1 6/2004 Leitner et al.
2004/0115586 A1 6/2004 Andreiko et al.
2004/0122436 A1 6/2004 Grimm
2004/0122439 A1 6/2004 Dwyer et al.
2004/0128026 A1 7/2004 Harris et al.
2004/0133276 A1 7/2004 Lang et al.
2004/0138754 A1 7/2004 Lang et al.
2004/0143336 A1 7/2004 Burkinshaw
2004/0147927 A1 7/2004 Tsougarakis et al.
2004/0148026 A1 7/2004 Bonutti
2004/0153079 A1 8/2004 Tsougarakis et al.
2004/0153087 A1 8/2004 Sanford et al.
2004/0158254 A1 8/2004 Eisermann
2004/0162619 A1 8/2004 Blaylock et al.
2004/0167390 A1 8/2004 Alexander et al.
2004/0171924 A1 9/2004 Mire et al.
2004/0172137 A1 9/2004 Blaylock et al.
2004/0181144 A1 9/2004 Cinquin et al.
2004/0193169 A1 9/2004 Schon et al.
2004/0204644 A1 10/2004 Tsougarakis et al.
2004/0204760 A1 10/2004 Fitz et al.
2004/0212586 A1 10/2004 Denny
2004/0220583 A1 11/2004 Pieczynski et al.
2004/0236341 A1 11/2004 Petersen
2004/0236424 A1 11/2004 Berez et al.
2004/0243481 A1 12/2004 Bradbury et al.
2004/0254584 A1 12/2004 Sarin et al.
2004/0260301 A1 12/2004 Lionberger et al.
2005/0008887 A1 1/2005 Haymann et al.
2005/0010227 A1 1/2005 Paul
2005/0010300 A1 1/2005 Disilvestro et al.
2005/0015022 A1 1/2005 Richard et al.
2005/0019664 A1 1/2005 Matsumoto
2005/0027303 A1 2/2005 Lionberger et al.
2005/0027361 A1 2/2005 Reiley
2005/0043806 A1 2/2005 Cook et al.
2005/0043837 A1 2/2005 Rubbert et al.
2005/0049524 A1 3/2005 Lefevre et al.
2005/0049603 A1 3/2005 Calton et al.
2005/0059873 A1 3/2005 Glozman et al.
2005/0060040 A1 3/2005 Auxepaules et al.
2005/0065628 A1 3/2005 Roose
2005/0070897 A1 3/2005 Petersen
2005/0071015 A1 3/2005 Sekel
2005/0075641 A1 4/2005 Singhatat et al.
2005/0096535 A1 5/2005 de la Barrera
2005/0113841 A1 5/2005 Sheldon et al.
2005/0113846 A1 5/2005 Carson
2005/0119664 A1 6/2005 Carignan et al.
2005/0131662 A1 6/2005 Ascenzi et al.
2005/0137708 A1 6/2005 Clark
2005/0148843 A1 7/2005 Roose
2005/0149042 A1 7/2005 Metzger
2005/0171545 A1 8/2005 Walsh et al.
2005/0177245 A1 8/2005 Leatherbury et al.
2005/0203536 A1 9/2005 Laffargue et al.
2005/0203540 A1 9/2005 Broyles
2005/0209605 A1 9/2005 Grimm et al.
2005/0216305 A1 9/2005 Funderud
2005/0222571 A1 10/2005 Ryan
2005/0222573 A1 10/2005 Branch et al.
2005/0228393 A1 10/2005 Williams et al.
2005/0234461 A1 10/2005 Burdulis et al.
2005/0234465 A1 10/2005 McCombs et al.
2005/0234468 A1 10/2005 Carson
2005/0240195 A1 10/2005 Axelson et al.
2005/0240267 A1 10/2005 Randall et al.
2005/0244239 A1 11/2005 Shimp
2005/0245934 A1 11/2005 Tuke et al.
2005/0245936 A1 11/2005 Tuke et al.
2005/0251147 A1 11/2005 Novak
2005/0267353 A1 12/2005 Marquart et al.
2005/0267485 A1 12/2005 Cordes et al.
2005/0267584 A1 12/2005 Burdulis et al.
2005/0273114 A1 12/2005 Novak
2005/0283252 A1 12/2005 Coon et al.
2005/0283253 A1 12/2005 Coon et al.
2006/0004284 A1 1/2006 Grunschlager et al.
2006/0015120 A1 1/2006 Richard et al.
2006/0030853 A1 2/2006 Haines

(56) References Cited

U.S. PATENT DOCUMENTS

2006/0038520 A1 2/2006 Negoro et al.
2006/0052725 A1 3/2006 Santilli
2006/0058803 A1 3/2006 Cuckler et al.
2006/0058884 A1 3/2006 Aram et al.
2006/0058886 A1 3/2006 Wozencroft
2006/0089621 A1 4/2006 Fard
2006/0093988 A1 5/2006 Swaelens et al.
2006/0094951 A1 5/2006 Dean et al.
2006/0095044 A1 5/2006 Grady et al.
2006/0100832 A1 5/2006 Bowman
2006/0105011 A1 5/2006 Sun et al.
2006/0111722 A1 5/2006 Bouadi
2006/0122616 A1 6/2006 Bennett et al.
2006/0122618 A1 6/2006 Claypool et al.
2006/0136058 A1 6/2006 Pietrzak
2006/0142657 A1 6/2006 Quaid et al.
2006/0147332 A1 7/2006 Jones et al.
2006/0149283 A1 7/2006 May et al.
2006/0155380 A1 7/2006 Clemow et al.
2006/0161165 A1 7/2006 Swanson
2006/0161167 A1 7/2006 Myers et al.
2006/0172263 A1 8/2006 Quadling et al.
2006/0178497 A1 8/2006 Gevaert et al.
2006/0184177 A1 8/2006 Echeverri
2006/0184250 A1 8/2006 Bandoh et al.
2006/0190086 A1 8/2006 Clemow et al.
2006/0192319 A1 8/2006 Solar
2006/0195111 A1 8/2006 Couture
2006/0195194 A1 8/2006 Gunther
2006/0195198 A1 8/2006 James
2006/0200158 A1 9/2006 Farling et al.
2006/0204932 A1 9/2006 Haymann et al.
2006/0210644 A1 9/2006 Levin
2006/0217808 A1 9/2006 Novak et al.
2006/0235421 A1 10/2006 Rosa et al.
2006/0241635 A1 10/2006 Stumpo et al.
2006/0241636 A1 10/2006 Novak et al.
2006/0271058 A1 11/2006 Ashton et al.
2006/0276796 A1 12/2006 Creger et al.
2006/0276797 A1 12/2006 Botimer
2006/0287733 A1 12/2006 Bonutti
2006/0287891 A1 12/2006 Grasso et al.
2006/0293681 A1 12/2006 Claypool et al.
2007/0015995 A1 1/2007 Lang et al.
2007/0016209 A1 1/2007 Ammann et al.
2007/0027680 A1 2/2007 Ashley et al.
2007/0039205 A1 2/2007 Erb et al.
2007/0043582 A1 2/2007 Peveto et al.
2007/0066917 A1 3/2007 Hodorek et al.
2007/0073137 A1 3/2007 Schoenefeld
2007/0083214 A1 4/2007 Duncan et al.
2007/0083266 A1 4/2007 Lang
2007/0100258 A1 5/2007 Shoham et al.
2007/0100450 A1 5/2007 Hodorek
2007/0100462 A1 5/2007 Lang et al.
2007/0106299 A1 5/2007 Manspeizer
2007/0118055 A1 5/2007 McCombs
2007/0118138 A1 5/2007 Seo et al.
2007/0118243 A1 5/2007 Schroeder et al.
2007/0142914 A1 6/2007 Jones et al.
2007/0150068 A1 6/2007 Dong et al.
2007/0156066 A1 7/2007 McGinley et al.
2007/0156171 A1 7/2007 Lang et al.
2007/0162038 A1 7/2007 Tuke
2007/0162039 A1 7/2007 Wozencroft
2007/0173946 A1 7/2007 Bonutti
2007/0173948 A1 7/2007 Meridew et al.
2007/0185498 A2 8/2007 Lavallee
2007/0191962 A1 8/2007 Jones et al.
2007/0198022 A1 8/2007 Lang et al.
2007/0203430 A1 8/2007 Lang et al.
2007/0203605 A1 8/2007 Melton et al.
2007/0219639 A1 9/2007 Otto et al.
2007/0219640 A1 9/2007 Steinberg
2007/0224238 A1 9/2007 Mansmann et al.
2007/0226986 A1 10/2007 Park et al.
2007/0233121 A1 10/2007 Carson et al.
2007/0233136 A1 10/2007 Wozencroft
2007/0233140 A1 10/2007 Metzger et al.
2007/0233141 A1 10/2007 Park et al.
2007/0233269 A1 10/2007 Steines et al.
2007/0233272 A1 10/2007 Boyce et al.
2007/0238069 A1 10/2007 Lovald et al.
2007/0239282 A1 10/2007 Caylor et al.
2007/0239481 A1 10/2007 DiSilvestro et al.
2007/0244487 A1 10/2007 Ammann et al.
2007/0250169 A1 10/2007 Lang
2007/0253617 A1 11/2007 Arata et al.
2007/0255288 A1 11/2007 Mahfouz et al.
2007/0255412 A1 11/2007 Hajaj et al.
2007/0262867 A1 11/2007 Westrick et al.
2007/0272747 A1 11/2007 Woods et al.
2007/0276224 A1 11/2007 Lang et al.
2007/0276400 A1 11/2007 Moore et al.
2007/0276501 A1 11/2007 Betz et al.
2007/0288029 A1 12/2007 Justin et al.
2007/0288030 A1 12/2007 Metzger et al.
2008/0009952 A1 1/2008 Hodge
2008/0015599 A1 1/2008 D'Alessio et al.
2008/0015603 A1 1/2008 Collazo
2008/0015604 A1 1/2008 Collazo
2008/0015605 A1* 1/2008 Collazo .......................... 606/87
2008/0021299 A1 1/2008 Meulink
2008/0021494 A1 1/2008 Schmelzeisen-Redeker et al.
2008/0021567 A1 1/2008 Meulink et al.
2008/0027563 A1 1/2008 Johnson et al.
2008/0033442 A1 2/2008 Amiot et al.
2008/0039850 A1 2/2008 Rowley et al.
2008/0051799 A1 2/2008 Bonutti
2008/0051910 A1 2/2008 Kammerzell et al.
2008/0058945 A1 3/2008 Hajaj et al.
2008/0058947 A1 3/2008 Earl et al.
2008/0062183 A1 3/2008 Swaelens
2008/0065225 A1 3/2008 Wasielewski et al.
2008/0094396 A1 4/2008 Sabczynsdi et al.
2008/0097451 A1 4/2008 Chen et al.
2008/0112996 A1 5/2008 Harlow et al.
2008/0114370 A1 5/2008 Schoenefeld
2008/0133022 A1 6/2008 Caylor
2008/0140081 A1 6/2008 Heavener et al.
2008/0140209 A1 6/2008 Iannotti et al.
2008/0140213 A1 6/2008 Ammann et al.
2008/0146969 A1 6/2008 Kurtz
2008/0147072 A1 6/2008 Park et al.
2008/0147073 A1 6/2008 Ammann et al.
2008/0147074 A1 6/2008 Ammann et al.
2008/0161815 A1 7/2008 Schoenefeld et al.
2008/0161816 A1 7/2008 Stevens et al.
2008/0172125 A1 7/2008 Ek
2008/0195099 A1 8/2008 Minas
2008/0195107 A1 8/2008 Cuckler et al.
2008/0195108 A1 8/2008 Bhatnagar et al.
2008/0195109 A1 8/2008 Hunter et al.
2008/0195216 A1 8/2008 Philipp
2008/0200926 A1 8/2008 Verard et al.
2008/0208200 A1 8/2008 Crofford
2008/0208353 A1 8/2008 Kumar et al.
2008/0215059 A1 9/2008 Carignan et al.
2008/0230422 A1 9/2008 Pleil et al.
2008/0234664 A1 9/2008 May et al.
2008/0234683 A1 9/2008 May
2008/0234685 A1 9/2008 Gjerde
2008/0234833 A1 9/2008 Bandoh et al.
2008/0243127 A1 10/2008 Lang et al.
2008/0255674 A1 10/2008 Rahaman et al.
2008/0257363 A1 10/2008 Schoenefeld et al.
2008/0262500 A1 10/2008 Collazo
2008/0262624 A1 10/2008 White et al.
2008/0269596 A1 10/2008 Revie et al.
2008/0269906 A1 10/2008 Iannotti et al.
2008/0275452 A1 11/2008 Lang et al.
2008/0281328 A1 11/2008 Lang et al.
2008/0281329 A1 11/2008 Fitz et al.
2008/0281426 A1 11/2008 Fitz et al.

(56) References Cited

U.S. PATENT DOCUMENTS

2008/0287926 A1 11/2008 Abou El Kheir
2008/0287954 A1 11/2008 Kunz et al.
2008/0294170 A1 11/2008 O'Brien
2008/0294266 A1 11/2008 Steinberg
2008/0300600 A1 12/2008 Guelat et al.
2008/0306485 A1 12/2008 Coon et al.
2008/0306558 A1 12/2008 Hakki
2008/0312659 A1 12/2008 Metzger et al.
2008/0319448 A1 12/2008 Lavallee et al.
2009/0012526 A1 1/2009 Fletcher
2009/0018546 A1 1/2009 Daley
2009/0018666 A1 1/2009 Grundei et al.
2009/0024131 A1* 1/2009 Metzger et al. ................ 606/88
2009/0024169 A1 1/2009 Triplett et al.
2009/0043556 A1 2/2009 Axelson et al.
2009/0048618 A1 2/2009 Harrison et al.
2009/0076371 A1 3/2009 Lang et al.
2009/0076512 A1 3/2009 Ammann et al.
2009/0076520 A1 3/2009 Choi
2009/0076555 A1 3/2009 Lowry et al.
2009/0082770 A1 3/2009 Worner et al.
2009/0082774 A1 3/2009 Oti et al.
2009/0087276 A1 4/2009 Rose
2009/0088674 A1 4/2009 Caillouette et al.
2009/0088753 A1 4/2009 Aram et al.
2009/0088754 A1 4/2009 Aker et al.
2009/0088755 A1 4/2009 Aker et al.
2009/0088758 A1 4/2009 Bennett
2009/0088759 A1 4/2009 Aram et al.
2009/0088760 A1 4/2009 Aram et al.
2009/0088761 A1 4/2009 Roose et al.
2009/0088763 A1 4/2009 Aram et al.
2009/0088865 A1 4/2009 Brehm
2009/0088866 A1 4/2009 Case
2009/0089034 A1 4/2009 Penney et al.
2009/0089081 A1 4/2009 Haddad
2009/0093815 A1 4/2009 Fletcher et al.
2009/0093816 A1 4/2009 Roose et al.
2009/0096613 A1 4/2009 Westrick
2009/0099567 A1 4/2009 Zajac
2009/0105837 A1 4/2009 Lafosse et al.
2009/0116621 A1 5/2009 Yuan et al.
2009/0118736 A1 5/2009 Kreuzer
2009/0118769 A1 5/2009 Sixto, Jr. et al.
2009/0131941 A1 5/2009 Park et al.
2009/0131942 A1 5/2009 Aker et al.
2009/0138020 A1 5/2009 Park et al.
2009/0149964 A1 6/2009 May et al.
2009/0149965 A1 6/2009 Quaid
2009/0149977 A1 6/2009 Schendel
2009/0151736 A1 6/2009 Belcher et al.
2009/0157083 A1 6/2009 Park et al.
2009/0163922 A1 6/2009 Meridew et al.
2009/0163923 A1 6/2009 Flett et al.
2009/0164024 A1 6/2009 Rudan et al.
2009/0177282 A1 7/2009 Bureau et al.
2009/0187193 A1 7/2009 Maroney et al.
2009/0209884 A1 8/2009 Van Vorhis et al.
2009/0209961 A1 8/2009 Ferrante et al.
2009/0222014 A1 9/2009 Bojarski et al.
2009/0222015 A1 9/2009 Park et al.
2009/0222016 A1 9/2009 Park et al.
2009/0222103 A1 9/2009 Fitz et al.
2009/0226068 A1 9/2009 Fitz et al.
2009/0228016 A1 9/2009 Alvarez et al.
2009/0234360 A1 9/2009 Alexander
2009/0248044 A1 10/2009 Amiot et al.
2009/0250413 A1 10/2009 Hoeppner
2009/0254093 A1 10/2009 White et al.
2009/0254367 A1 10/2009 Belcher et al.
2009/0259312 A1 10/2009 Shterling et al.
2009/0270868 A1 10/2009 Park et al.
2009/0274350 A1 11/2009 Pavlovskaia et al.
2009/0287217 A1 11/2009 Ammann et al.
2009/0287309 A1 11/2009 Walch et al.
2009/0306676 A1 12/2009 Lang et al.
2009/0307893 A1 12/2009 Burdulis, Jr. et al.
2009/0318836 A1 12/2009 Stone et al.
2009/0318921 A1 12/2009 White et al.
2010/0010493 A1 1/2010 Dower
2010/0016984 A1 1/2010 Trabish
2010/0016986 A1 1/2010 Trabish
2010/0023015 A1 1/2010 Park
2010/0030231 A1 2/2010 Revie et al.
2010/0036404 A1 2/2010 Yi et al.
2010/0042105 A1 2/2010 Park et al.
2010/0049195 A1 2/2010 Park et al.
2010/0057088 A1 3/2010 Shah
2010/0076439 A1 3/2010 Hatch
2010/0076505 A1 3/2010 Borja
2010/0076563 A1 3/2010 Otto et al.
2010/0076571 A1 3/2010 Hatch
2010/0082034 A1 4/2010 Remia
2010/0082035 A1 4/2010 Keefer
2010/0082067 A1 4/2010 Kondrashov
2010/0087829 A1 4/2010 Metzger et al.
2010/0094295 A1 4/2010 Schnieders et al.
2010/0105011 A1 4/2010 Karkar et al.
2010/0121334 A1 5/2010 Couture et al.
2010/0121335 A1 5/2010 Penenberg et al.
2010/0137869 A1 6/2010 Borja et al.
2010/0137924 A1 6/2010 Tuke et al.
2010/0145343 A1 6/2010 Johnson et al.
2010/0145344 A1 6/2010 Jordan et al.
2010/0152782 A1 6/2010 Stone et al.
2010/0160917 A1 6/2010 Fitz et al.
2010/0160919 A1 6/2010 Axelson, Jr. et al.
2010/0168752 A1 7/2010 Edwards
2010/0168754 A1 7/2010 Fitz et al.
2010/0168857 A1 7/2010 Hatch
2010/0168866 A1 7/2010 Shih
2010/0179663 A1 7/2010 Steinberg
2010/0185202 A1 7/2010 Lester et al.
2010/0191244 A1 7/2010 White et al.
2010/0198067 A1 8/2010 Mahfouz et al.
2010/0198224 A1 8/2010 Metzger et al.
2010/0212138 A1 8/2010 Carroll et al.
2010/0217109 A1 8/2010 Belcher
2010/0217270 A1 8/2010 Polinski et al.
2010/0217336 A1 8/2010 Crawford et al.
2010/0217338 A1 8/2010 Carroll et al.
2010/0217399 A1 8/2010 Groh
2010/0228257 A1 9/2010 Bonutti
2010/0249657 A1 9/2010 Nycz et al.
2010/0249796 A1 9/2010 Nycz
2010/0256649 A1 10/2010 Capsal et al.
2010/0262150 A1 10/2010 Lian
2010/0274253 A1 10/2010 Ure
2010/0281678 A1 11/2010 Burdulis, Jr. et al.
2010/0286700 A1 11/2010 Snider et al.
2010/0291401 A1 11/2010 Medina et al.
2010/0292743 A1 11/2010 Singhal et al.
2010/0298894 A1 11/2010 Bojarski et al.
2010/0305574 A1 12/2010 Fitz et al.
2010/0318088 A1 12/2010 Warne et al.
2010/0324692 A1 12/2010 Uthgenannt et al.
2011/0004317 A1 1/2011 Hacking et al.
2011/0008754 A1 1/2011 Bassett et al.
2011/0009869 A1 1/2011 Marino et al.
2011/0014081 A1 1/2011 Jones et al.
2011/0015636 A1 1/2011 Katrana et al.
2011/0015639 A1 1/2011 Metzger et al.
2011/0015752 A1 1/2011 Meridew
2011/0016690 A1 1/2011 Narainasamy et al.
2011/0022049 A1 1/2011 Huebner et al.
2011/0022174 A1 1/2011 Holdstein et al.
2011/0029088 A1 2/2011 Rauscher et al.
2011/0029091 A1 2/2011 Bojarski et al.
2011/0029093 A1 2/2011 Bojarski et al.
2011/0029116 A1 2/2011 Jordan et al.
2011/0035012 A1 2/2011 Linares
2011/0040303 A1 2/2011 Iannotti
2011/0040334 A1 2/2011 Kaes et al.
2011/0046735 A1 2/2011 Metzger et al.

(56) References Cited

U.S. PATENT DOCUMENTS

2011/0054478 A1 3/2011 Vanasse et al.
2011/0066193 A1 3/2011 Lang et al.
2011/0066245 A1 3/2011 Lang et al.
2011/0071528 A1 3/2011 Carson
2011/0071529 A1 3/2011 Carson
2011/0071530 A1 3/2011 Carson
2011/0071532 A1 3/2011 Carson
2011/0071533 A1 3/2011 Metzger et al.
2011/0071581 A1 3/2011 Lang et al.
2011/0071802 A1 3/2011 Bojarski et al.
2011/0087332 A1 4/2011 Bojarski et al.
2011/0092804 A1 4/2011 Schoenefeld et al.
2011/0093086 A1 4/2011 Witt et al.
2011/0106093 A1 5/2011 Romano et al.
2011/0106254 A1 5/2011 Abel et al.
2011/0125264 A1 5/2011 Bagga et al.
2011/0125284 A1 5/2011 Gabbrielli et al.
2011/0130795 A1 6/2011 Ball
2011/0151027 A1 6/2011 Clineff et al.
2011/0151259 A1 6/2011 Jarman-Smith et al.
2011/0153025 A1 6/2011 McMinn
2011/0160736 A1 6/2011 Meridew et al.
2011/0160867 A1 6/2011 Meridew et al.
2011/0166578 A1 7/2011 Stone et al.
2011/0172672 A1 7/2011 Dubeau et al.
2011/0177590 A1 7/2011 Clyne et al.
2011/0184419 A1 7/2011 Meridew et al.
2011/0184526 A1 7/2011 White et al.
2011/0190899 A1 8/2011 Pierce et al.
2011/0190901 A1 8/2011 Weissberg et al.
2011/0213376 A1 9/2011 Maxson et al.
2011/0214279 A1 9/2011 Park et al.
2011/0218545 A1 9/2011 Catanzarite et al.
2011/0224674 A1 9/2011 White et al.
2011/0238071 A1 9/2011 Fernandez-Scoma
2011/0245835 A1 10/2011 Dodds et al.
2011/0251617 A1 10/2011 Ammann et al.
2011/0257657 A1 10/2011 Turner et al.
2011/0269100 A1 11/2011 Furrer et al.
2011/0275032 A1 11/2011 Tardieu et al.
2011/0276145 A1 11/2011 Carignan et al.
2011/0282473 A1 11/2011 Pavlovskaia et al.
2011/0295887 A1 12/2011 Palmese et al.
2011/0313424 A1 12/2011 Bono et al.
2011/0319745 A1 12/2011 Frey
2012/0010619 A1 1/2012 Barsoum
2012/0010710 A1 1/2012 Frigg
2012/0010711 A1 1/2012 Antonyshyn et al.
2012/0029345 A1 2/2012 Mahfouz et al.
2012/0029520 A1 2/2012 Lang et al.
2012/0041445 A1 2/2012 Roose et al.
2012/0041446 A1 2/2012 Wong et al.
2012/0041564 A1 2/2012 Landon
2012/0065640 A1 3/2012 Metzger et al.
2012/0078254 A1 3/2012 Ashby et al.
2012/0078258 A1 3/2012 Lo et al.
2012/0078259 A1 3/2012 Meridew
2012/0089595 A1 4/2012 Jaecksch
2012/0101586 A1 4/2012 Carson
2012/0109137 A1 5/2012 Iannotti et al.
2012/0109138 A1 5/2012 Meridew et al.
2012/0109226 A1 5/2012 Iannotti et al.
2012/0116203 A1 5/2012 Vancraen et al.
2012/0123422 A1 5/2012 Agnihotri et al.
2012/0130382 A1 5/2012 Iannotti et al.
2012/0136365 A1 5/2012 Iannotti et al.
2012/0141034 A1 6/2012 Iannotti et al.
2012/0143197 A1 6/2012 Lang et al.
2012/0143267 A1 6/2012 Iannotti et al.
2012/0150242 A1 6/2012 Mannion
2012/0158002 A1 6/2012 Carignan et al.
2012/0165954 A1 6/2012 Nimal
2012/0192401 A1 8/2012 Pavlovskaia et al.
2012/0209276 A1 8/2012 Schuster
2012/0215225 A1 8/2012 Philippon et al.
2012/0215310 A1 8/2012 Sharp et al.
2012/0221017 A1 8/2012 Bonutti
2012/0226283 A1 9/2012 Meridew et al.
2012/0232596 A1 9/2012 Ribeiro
2012/0245587 A1 9/2012 Fang et al.
2012/0259335 A1 10/2012 Scifert et al.
2012/0265208 A1 10/2012 Smith
2012/0271131 A1 10/2012 Kling et al.
2012/0271314 A1 10/2012 Stemniski et al.
2012/0271366 A1 10/2012 Katrana et al.
2012/0276509 A1 11/2012 Iannotti et al.
2012/0277751 A1 11/2012 Catanzarite et al.
2012/0289965 A1 11/2012 Gelaude et al.
2012/0296339 A1 11/2012 Iannotti et al.
2012/0303004 A1 11/2012 Uthgenannt et al.
2012/0303033 A1 11/2012 Weiner et al.
2012/0310364 A1 12/2012 Li et al.
2012/0310399 A1 12/2012 Metzger
2012/0316564 A1 12/2012 Serbousek et al.
2012/0323246 A1 12/2012 Catanzarite et al.
2012/0323282 A1 12/2012 Brianza et al.
2012/0323323 A1 12/2012 Vargas et al.
2013/0001121 A1 1/2013 Metzger
2013/0006250 A1 1/2013 Metzger et al.
2013/0018483 A1 1/2013 Li et al.
2013/0035766 A1 2/2013 Meridew
2013/0046310 A1 2/2013 Ranawat et al.
2013/0056912 A1 3/2013 O'Neill et al.
2013/0060253 A1 3/2013 Couture et al.
2013/0072940 A1 3/2013 Dawood et al.
2013/0085500 A1 4/2013 Meridew et al.
2013/0085590 A1 4/2013 Bryan et al.
2013/0119579 A1 5/2013 Iannotti et al.
2013/0123850 A1 5/2013 Schoenefeld et al.
2013/0131681 A1 5/2013 Katrana et al.
2013/0144392 A1 6/2013 Hughes
2013/0197528 A1 8/2013 Zakaria et al.
2013/0197529 A1 8/2013 Metzger et al.
2013/0197687 A1 8/2013 Pavlovskaia et al.
2013/0218163 A1 8/2013 Frey
2013/0245631 A1 9/2013 Bettenga
2013/0245801 A1 9/2013 Schroeder
2013/0261503 A1 10/2013 Sherman et al.
2013/0264749 A1 10/2013 Jones et al.
2013/0268085 A1 10/2013 Dong et al.
2013/0289730 A1 10/2013 Gabriel et al.
2013/0317511 A1 11/2013 Bojarski et al.
2013/0338673 A1 12/2013 Keppler
2014/0005672 A1 1/2014 Edwards et al.
2014/0012266 A1 1/2014 Bonin, JR. et al.
2014/0052270 A1 2/2014 Witt et al.
2014/0081275 A1 3/2014 Metzger et al.
2014/0088724 A1 3/2014 Meridew
2014/0094816 A1 4/2014 White et al.
2014/0100578 A1 4/2014 Metzger et al.
2014/0107651 A1 4/2014 Meridew et al.
2014/0107654 A1 4/2014 Kehres et al.
2014/0107715 A1 4/2014 Heilman et al.
2014/0127211 A1 5/2014 Geles et al.
2014/0135775 A1 5/2014 Maxson et al.
2014/0163564 A1 6/2014 Bollinger
2014/0163565 A1 6/2014 Bollinger
2014/0188119 A1 7/2014 Catanzarite et al.
2014/0222157 A1 8/2014 Al Hares et al.
2014/0243833 A1 8/2014 Smith
2014/0257304 A1 9/2014 Eash
2014/0257508 A1 9/2014 Bojarski et al.
2014/0276854 A1 9/2014 Schoenefeld et al.
2014/0276856 A1 9/2014 Schoenefeld
2014/0276870 A1 9/2014 Eash
2014/0276873 A1 9/2014 Meridew et al.
2014/0324058 A1 10/2014 Metzger et al.
2014/0378979 A1 12/2014 Stone et al.
2015/0088293 A1 3/2015 Metzger

FOREIGN PATENT DOCUMENTS

CA 2505371 A1 5/2004
CA 2505419 A1 6/2004

(56) References Cited

FOREIGN PATENT DOCUMENTS

| | | | |
|---|---|---|---|
| CA | 2506849 | A1 | 6/2004 |
| CA | 2546958 | A1 | 6/2005 |
| CA | 2546965 | A1 | 6/2005 |
| CA | 2588907 | A1 | 6/2006 |
| CA | 2590534 | A1 | 6/2006 |
| CN | 1630495 | A | 6/2005 |
| CN | 1728976 | A | 2/2006 |
| CN | 1729483 | A | 2/2006 |
| CN | 1729484 | A | 2/2006 |
| CN | 1913844 | A | 2/2007 |
| CN | 101111197 | A | 1/2008 |
| CN | 102038553 | A | 5/2011 |
| CN | 102335742 | A | 2/2012 |
| DE | 3447365 | A1 | 7/1986 |
| DE | 04219939 | | 12/1993 |
| DE | 4421153 | A1 | 12/1995 |
| DE | 10341187 | A1 | 3/2005 |
| DE | 102009028503 | A1 | 2/2011 |
| DE | 102011082902 | A1 | 3/2012 |
| DE | 102012205820 | A1 | 10/2012 |
| DE | 112010003901 | T5 | 11/2012 |
| EP | 0114505 | A1 | 8/1984 |
| EP | 0255797 | A1 | 2/1988 |
| EP | 0326768 | A2 | 8/1989 |
| EP | 0579868 | A2 | 1/1994 |
| EP | 0591985 | A1 | 4/1994 |
| EP | 0645984 | A1 | 4/1995 |
| EP | 0650706 | A1 | 5/1995 |
| EP | 0916324 | A2 | 5/1999 |
| EP | 1321107 | A1 | 6/2003 |
| EP | 1327424 | A1 | 7/2003 |
| EP | 1437102 | A1 | 7/2004 |
| EP | 01486900 | A1 | 12/2004 |
| EP | 1634551 | A2 | 3/2006 |
| EP | 1852072 | A2 | 7/2007 |
| EP | 1832239 | A1 | 9/2007 |
| EP | 2029061 | A2 | 3/2009 |
| EP | 2168507 | A2 | 3/2010 |
| EP | 2303146 | A1 | 4/2011 |
| EP | 2303192 | A1 | 4/2011 |
| EP | 2352445 | A1 | 8/2011 |
| EP | 2396741 | A1 | 12/2011 |
| EP | 2398381 | A1 | 12/2011 |
| EP | 2403437 | A2 | 1/2012 |
| EP | 2491873 | A2 | 8/2012 |
| EP | 2502582 | A1 | 9/2012 |
| EP | 2709568 | A1 | 3/2014 |
| FR | 2659226 | A1 | 9/1991 |
| FR | 2721195 | A1 | 12/1995 |
| FR | 2768916 | A1 | 4/1999 |
| FR | 2979817 | A1 | 3/2013 |
| GB | 2094590 | A | 9/1982 |
| GB | 2197790 | A | 6/1988 |
| GB | 2442441 | A | 4/2008 |
| GB | 2447702 | A | 9/2008 |
| GB | 2483980 | A | 3/2012 |
| GB | 2486390 | A | 6/2012 |
| GB | 2490220 | A | 10/2012 |
| GB | 2491526 | A | 12/2012 |
| JP | 59157715 | A | 9/1984 |
| JP | 60231208 | A | 11/1985 |
| JP | 6-233790 | A | 8/1994 |
| JP | 2000245758 | A | 9/2000 |
| JP | 2005-218861 | A | 8/2005 |
| JP | 2009514612 | A | 4/2009 |
| JP | 2011505080 | A | 2/2011 |
| JP | 2011527885 | A | 11/2011 |
| KR | 20050072500 | A | 7/2005 |
| KR | 20050084024 | A | 8/2005 |
| RU | 2083179 | C1 | 7/1997 |
| RU | 2113182 | C1 | 6/1998 |
| RU | 2125835 | C1 | 2/1999 |
| RU | 2138223 | C1 | 9/1999 |
| RU | 2175534 | C2 | 11/2001 |
| RU | 2187975 | C1 | 8/2002 |
| RU | 2218242 | C2 | 12/2003 |
| TW | 231755 | | 5/2005 |
| WO | WO-8807840 | A1 | 10/1988 |
| WO | WO-9107139 | A1 | 5/1991 |
| WO | WO-9325157 | A1 | 12/1993 |
| WO | WO-9528688 | A1 | 10/1995 |
| WO | WO-9952473 | A1 | 10/1999 |
| WO | WO-9959106 | A1 | 11/1999 |
| WO | WO-0170142 | A1 | 9/2001 |
| WO | WO-0184479 | A1 | 11/2001 |
| WO | WO-0217821 | A2 | 3/2002 |
| WO | WO-0226145 | | 4/2002 |
| WO | WO-0236024 | A1 | 5/2002 |
| WO | WO-02096268 | A2 | 12/2002 |
| WO | WO-03051210 | A2 | 6/2003 |
| WO | WO-03051211 | A1 | 6/2003 |
| WO | WO-2004032806 | A1 | 4/2004 |
| WO | WO-2004049981 | A2 | 6/2004 |
| WO | WO-2004051301 | A2 | 6/2004 |
| WO | WO-2004078069 | A2 | 9/2004 |
| WO | WO-2005051233 | A2 | 6/2005 |
| WO | WO-2005051239 | A1 | 6/2005 |
| WO | WO-2005051240 | A1 | 6/2005 |
| WO | WO-2005077039 | A2 | 8/2005 |
| WO | WO-2006058057 | A2 | 6/2006 |
| WO | WO-2006060795 | A1 | 6/2006 |
| WO | WO-2006092600 | A1 | 9/2006 |
| WO | WO-2006127486 | A2 | 11/2006 |
| WO | WO-2006134345 | A1 | 12/2006 |
| WO | WO-2006136955 | A1 | 12/2006 |
| WO | WO-2007041375 | A2 | 4/2007 |
| WO | WO-2007053572 | A2 | 5/2007 |
| WO | WO-2007062079 | A2 | 5/2007 |
| WO | WO-2007092841 | A2 | 8/2007 |
| WO | WO-2007137327 | A1 | 12/2007 |
| WO | WO-2007145937 | A2 | 12/2007 |
| WO | WO-2008014618 | A1 | 2/2008 |
| WO | WO-2008021494 | A2 | 2/2008 |
| WO | WO-2008040961 | A1 | 4/2008 |
| WO | WO-2008044055 | A1 | 4/2008 |
| WO | WO-2008091358 | A1 | 7/2008 |
| WO | WO-2008101090 | A2 | 8/2008 |
| WO | WO-2008109751 | A1 | 9/2008 |
| WO | WO-2008112996 | A1 | 9/2008 |
| WO | WO-2008140748 | A1 | 11/2008 |
| WO | WO-2009001083 | A1 | 12/2008 |
| WO | WO-2009001109 | A1 | 12/2008 |
| WO | WO-2009025783 | A1 | 2/2009 |
| WO | WO-2009073781 | A2 | 6/2009 |
| WO | WO-2009129063 | A1 | 10/2009 |
| WO | WO-2009129067 | A1 | 10/2009 |
| WO | WO-2010033431 | A1 | 3/2010 |
| WO | WO-2010093902 | A1 | 8/2010 |
| WO | WO-2010096553 | A1 | 8/2010 |
| WO | WO-2010096557 | A2 | 8/2010 |
| WO | WO-2010124164 | A1 | 10/2010 |
| WO | WO-2010129870 | A1 | 11/2010 |
| WO | WO-2010144705 | A1 | 12/2010 |
| WO | WO-2010148103 | A1 | 12/2010 |
| WO | WO-2010150223 | A1 | 12/2010 |
| WO | WO-2011018458 | A1 | 2/2011 |
| WO | WO-2011041398 | A1 | 4/2011 |
| WO | WO-2011060536 | A1 | 5/2011 |
| WO | WO-2011019797 | A3 | 7/2011 |
| WO | WO-2011080260 | A1 | 7/2011 |
| WO | WO-2011106711 | A1 | 9/2011 |
| WO | WO-2011109260 | A1 | 9/2011 |
| WO | WO-2011110374 | A1 | 9/2011 |
| WO | WO-2011117644 | A2 | 9/2011 |
| WO | WO-2012006444 | A2 | 1/2012 |
| WO | WO-2012033821 | A1 | 3/2012 |
| WO | WO-2012058344 | A1 | 5/2012 |
| WO | WO-2012061042 | A1 | 5/2012 |
| WO | WO-2012058353 | A4 | 6/2012 |
| WO | WO-2012058355 | A4 | 7/2012 |
| WO | WO-2012058349 | A4 | 8/2012 |
| WO | WO-2012116206 | A1 | 8/2012 |

(56) References Cited

FOREIGN PATENT DOCUMENTS

WO WO-2012158917 A1 11/2012
WO WO-2012173929 A1 12/2012
WO WO-2012174008 A1 12/2012

OTHER PUBLICATIONS

International Preliminary Report on Patentability mailed Sep. 6, 2013 for PCT/US2012/026356 claiming benefit of U.S. Appl. No. 13/041,883, filed Mar. 7, 2011.
International Search Report and Written Opinion mailed Oct. 14, 2013 for PCT/US2013/057097 claiming benefit of U.S. Appl. No. 13/597,478, filed Aug. 29, 2012.
"Comprehensive® Reverse Shoulder System Surgical Technique," Biomet Orthopedics brochure (2009-2012), 48 pages.
"Comprehensive® Reverse Shoulder System Technical Design Features," Biomet Orthopedics brochure (2009), 3 pages.
"Comprehensive® Reverse Shoulder System," Biomet Orthopedics brochure (2009), 8 pages.
"Comprehensive® Shoulder System Surgical Technique," Biomet Orthopedics brochure (2007), pp. 1-53.
"Comprehensive® Total Shoulder System," Biomet Orthopedics brochure (2011), 4 pages.
Friedman, R.J. et al., "The Use of Computerized Tomography in the Measurement of Glenoid Version", Journal of Bone & Joint Surgery Am. (JBJS) 1992;74:1032-1037 (Aug. 1992).
International Search Report and Written Opinion mailed Dec. 18, 2012 for PCT/US2012/059189, which claims benefit of U.S. Appl. No. 13/597,478, filed Aug. 29, 2011.
International Search Report and Written Opinion mailed Feb. 6, 2013 for PCT/US2012/060842, which claims benefit of U.S. Appl. No. 13/653,868, filed Oct. 17, 2012.
International Search Report and Written Opinion mailed Feb. 6, 2013 for PCT/US2012/060854, which claims benefit of U.S. Appl. No. 13/653,893, filed Oct. 17, 2012.
International Search Report and Written Opinion mailed Nov. 15, 2012, for PCT/US2012/052853, which claims benefit of U.S. Appl. No. 13/221,968, filed Aug. 31, 2011.
International Search Report mailed Oct. 23, 2012, for PCT/US2012/041893, which claims benefit of U.S. Appl. No. 61/496,177, filed Jun. 13, 2011.
Invitation to Pay Additional Fees mailed Feb. 6, 2013 for PCT/US2012/060848, which claims benefit of U.S. Appl. No. 13/653,878, filed Oct. 17, 2012.
Invitation to Pay Additional Fees mailed Feb. 7, 2013 for PCT/US2012/060853, which claims benefit of U.S. Appl. No. 13/653,893, filed Oct. 17, 2012.
International Preliminary Report on Patentability and Written Opinion mailed Apr. 24, 2014 for PCT/US2012/059189 claiming benefit of U.S. Appl. No. 13/597,478, filed Aug. 29, 2012.
International Preliminary Report on Patentability and Written Opinion mailed Mar. 13, 2014 for PCT/US2012/052853 claiming benefit of U.S. Appl. No. 13/221,968, filed Aug. 31, 2011.
International Search Report and Written Opinion mailed Apr. 14, 2014 for PCT/US2013/067505 claiming benefit of U.S. Appl. No. 13/718,129, filed Dec. 18, 2012.
Invitation to Pay Additional Fees mailed Feb. 6, 2014 for PCT/US2013/067505, which claims benefit of U.S. Appl. No. 13/718,129, filed Dec. 18, 2012.
Signature™ Personalized Patient Care, Surgical Technique Addendum Vanguard® Complete Knee System, Biomet® Orthopedics Brochure, (2011), p. 1-32.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (Oct. 31, 1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (Dec. 31, 2008) pp. 1-25.
"Discovery® Elbow System," brochure. Biomet Orthopedics, Inc. (Nov. 30, 2007) 3 sheets.
"Hipsextant Instructions of Use." (2011) Surgical Planning Associates, Inc. 19 pages.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (Mar. 31, 2004) pp. 1-8 (12 sheets).
"Patient Matched PMI Implants, C.A.M.R.A. 3-D Imaging," brochure, Biomet, Inc. (Jan. 31, 1991) 6 pages.
"Regenerex® Tibial Cone Augment, Surgical Technique Addendum to the Vanguard® SSK Revision System," brochure. Biomet® Orthopedics. (Mar. 31, 2010) pp. 1-8 (12 sheets).
"Signature™ Personalized Patient Care, Surgical Technique Addendum to the Vanguard Knee System" brochure. Biomet® Orthopedics, Inc. (May 15, 2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (Aug. 31, 2010) pp. 1-25.
"Zimmer® UniSpacer® Knee System," brochure. (2005) Zimmer, Inc. 4 sheets.
Biomet "Oxford® Partial Knee" brochure, 8 pages (Feb. 2011).
Biomet "The Oxford® Partial Knee Surgical Technique," brochure, pp. 1-38, (Feb. 2010).
Biomet, "Oxford® Partial Knee Microplasty® Instrumentation Surgical Technique", brochure, pp. 1-54 (May 2011).
Birnbaum, Klaus, M.D., "Computer-Assisted Orthopedic Surgery With Individual Templates and Comparison to Conventional Method," Spine vol. 26, No. 4, pp. 365-370 (2001) Lippincott Williams & Wilkins, Inc.
Botha, Charl P., Technical Report: DeVide—The Delft Visualisation and Image processing Development Environment, pp. 1-49 (May 31, 2006).
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Great Britain Search Report mailed Dec. 21, 2011 for GB1116054.6, claiming benefit of U.S. Appl. No. 12/888,005, filed Sep. 22, 2010.
Haaker, R.G., et al., "Minimal-invasive navigiert implantierte unikondyläre Knieendoprothese," Orthopäde 2006 35:1073-1079 (Sep. 13, 2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report and Written Opinion mailed Jan. 5, 2012 for PCT/US2010/038845 claiming benefit of U.S. Appl. No. 12/486,992, filed Jun. 18, 2009.

(56) References Cited

OTHER PUBLICATIONS

International Preliminary Report on Patentability and Written Opinion for PCT/US2009/039578 mailed Oct. 28, 2010 claiming benefit of U.S. Appl. No. 12/103,834, filed Apr. 16, 2008.
International Preliminary Report on Patentability and Written Opinion mailed Dec. 22, 2011 for PCT/US2010/038177 claiming benefit of U.S. Appl. No. 12/483,807, filed Jun. 12, 2009.
International Preliminary Report on Patentability and Written Opinion mailed Oct. 28, 2010 for PCT/US2009/039507 claiming benefit of U.S. Appl. No. 12/103,824, filed Apr. 16, 2008.
International Preliminary Report on Patentability and Written Opinion mailed Sep. 7, 2012 for PCT/US2011/026333 claiming benefit of U.S. Appl. No. 12/714,023, filed Feb. 26, 2010.
International Preliminary Report on Patentability for PCT/US2007/013223 mailed Dec. 24, 2008 claiming benefit of U.S. Appl. No. 11/756,057, filed May 31, 2007.
International Preliminary Report on Patentability for PCT/US2010/050701 mailed Apr. 12, 2012 claiming benefit of U.S. Appl. No. 12/571,969, filed Oct. 1, 2009.
International Preliminary Report on Patentability mailed Aug. 25, 2011 for PCT/US2010/024073 filed Feb. 12, 2010, claiming benefit of U.S. Appl. No. 12/371,096, filed Feb. 13, 2009.
International Preliminary Report on Patentability mailed Mar. 31, 2011 for PCT/US2009/056670 claiming benefit of U.S. Appl. No. 12/211,407, filed Sep. 16, 2008.
International Preliminary Report on Patentability mailed Sep. 1, 2011 for PCT/US2010/024579 claiming benefit of U.S. Appl. No. 12/389,930, filed Feb. 20, 2009.
International Preliminary Report on Patentability mailed Sep. 1, 2011 for PCT/US2010/024584 claiming benefit of U.S. Appl. No. 12/389,901, filed Feb. 20, 2009.
International Search Report and Written Opinion for PCT/US2007/013223 mailed Nov. 26, 2007, claiming benefit of U.S. Appl. No. 11/756,057, filed May 31, 2007.
International Search Report and Written Opinion for PCT/US2009/039507 mailed Jul. 14, 2009, claiming benefit of U.S. Appl. No. 12/103,824.
International Search Report and Written Opinion for PCT/US2009/056670 mailed Mar. 2, 2010 claiming benefit of U.S. Appl. No. 12/211,407, filed Sep. 16, 2008.
International Search Report and Written Opinion mailed Apr. 22, 2010 for PCT/US2010/024579 claiming benefit of U.S. Appl. No. 12/389,930, filed Feb. 20, 2009.
International Search Report and Written Opinion mailed Aug. 19, 2010 for PCT/US2010/024584 claiming benefit of U.S. Appl. No. 12/389,901, filed Feb. 20, 2009.
International Search Report and Written Opinion mailed Aug. 24, 2010 for PCT/US2010/038177 claiming benefit of U.S. Appl. No. 12/483,807, filed Jun. 12, 2009.
International Search Report and Written Opinion mailed Aug. 9, 2011 for PCT/US2011/026333 claiming benefit of U.S. Appl. No. 12/714,023, filed Feb. 26, 2010.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Jul. 31, 2009 for PCT/US2009/039578 claiming benefit of U.S. Appl. No. 12/103,834, filed Apr. 16, 2008.
International Search Report and Written Opinion mailed Jun. 4, 2010 for PCT/US2010/024073 filed Feb. 12, 2010, claiming benefit of U.S. Appl. No. 12/371,096, filed Feb. 13, 2009.
International Search Report and Written Opinion mailed Mar. 5, 2012 for PCT/US2011/057300 claiming benefit of U.S. Appl. No. 12/938,905, filed Nov. 3, 2010.
International Search Report and Written Opinion mailed May 8, 2012 for PCT/US2012/026356 claiming benefit of U.S. Appl. No. 13/041,883, filed Mar. 7, 2011.
International Search Report and Written Opinion mailed May 9, 2011 for PCT/US2011/026412 claiming benefit of U.S. Appl. No. 12/872,663, filed Aug. 31, 2010.
International Search Report and Written Opinion mailed Oct. 5, 2010 for PCT/US2010/038845 claiming benefit of U.S. Appl. No. 12/486,992, filed Jun. 18, 2009.
International Search Report mailed Nov. 30, 2010 for PCT/EP2010/061630 filed Aug. 10, 2010 claiming benefit of DE102009028503.2 filed Aug. 13, 2009.
Invitation to Pay Additional Fees mailed May 3, 2011 for PCT/US2011/026333 claiming benefit of U.S. Appl. No. 12/714,023, filed Feb. 26, 2010.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Kelly, Todd C., M.D., "Role of Navigation in Total Hip Arthroplasty." The Journal of Bone & Joint Surgery(2009) pp. 153-158. vol. 91-A, Supplement 1.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Murphy, S.B., et al. "The Hip Sextant: Navigation of Acetabular Component Orientation Using a Mechanical Instrument," brochure. (2009) 1 page.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (Sep. 1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Radermacher, Klaus, et al. "Computer Assisted Orthopaedic Individual Templates." Clinical Orthopaedics and Related Research. (Sep. 1998) No. 354; pp. 28-38.

(56) References Cited

OTHER PUBLICATIONS

Schuller-Götzburg, P., et al., 3D-Implantatplanung und Stereolithographie-Implantatbohrschablonen, Stomatologie 101.3, pp. 55-59 (May 2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (Jul. 2006).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE . . . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

Supplementary European Search Report mailed Nov. 15, 2011 for EP07809326, which claims benefit of PCT/US2007/013223, filed Jun. 5, 2007; which claims benefit of U.S. Appl. No. 11/756,057, filed May 31, 2007.

Thoma, W., et al., "Endoprothetischen Versorgung des Kniegelenks auf der Basis eines 3D-computertomographischen Subtraktionversfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

International Preliminary Report on Patentability and Written Opinion mailed Jan. 3, 2014 for PCT/US2012/042081 claiming benefit of U.S. Appl. No. 13/493,509, filed Jun. 11, 2012.

International Preliminary Report on Patentability and Written Opinion mailed Nov. 28, 2013 for PCT/US2012/038351 claiming benefit of U.S. Appl. No. 13/111,007, filed May 19, 2011.

"Is Subchondroplasty® Right for Me?" Retrieved from <http://www.subchondroplasty.com/about_subchondroplasty/is_subchondroplasty_right_for_>. . . Jul. 1, 2013. 1 sheet.

"Subchondroplasty," Retrieved from <http://www.subchondroplasty.com/>. Jul. 1, 2013. 1 sheet.

Deakon, Timothy, MD, Posterior Cruciate Ligament Reconstruction Technique Using the Modular ACL/PCL Guide Rationale and Surgical Technique, Arthrotek®, a Biomet Company. (2003). (6 pages).

International Preliminary Report on Patentability and Written Opinion mailed May 8, 2014 for PCT/US2012/060842 claiming benefit of U.S. Appl. No. 13/653,868, filed Oct. 17, 2012.

International Preliminary Report on Patentability and Written Opinion mailed May 8, 2014 for PCT/US2012/060848 claiming benefit of U.S. Appl. No. 13/653,878, filed Oct. 17, 2012.

International Preliminary Report on Patentability and Written Opinion mailed May 8, 2014 for PCT/US2012/060853 claiming benefit of U.S. Appl. No. 13/653,886, filed Oct. 17, 2012.

International Preliminary Report on Patentability and Written Opinion mailed May 8, 2014 for PCT/US2012/060854 claiming benefit of U.S. Appl. No. 13/653,893, filed Oct. 17, 2012.

International Search Report and Written Opinion mailed Jun. 24, 2014 for PCT/US2014/022000 claiming benefit of U.S. Appl. No. 13/889,869, filed May 8, 2013.

International Search Report and Written Opinion mailed May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.

What is Subchondroplasty, Retrieved from <http://www.subchondroplasty.com/about_subchondroplasty/what_is_subchondroplasty.>, Jul. 1, 2013. 2 sheets.

International Preliminary Report on Patentability Report and Written Opinion mailed Sep. 4, 2014 for PCT/US2013/026875 claiming benefit of U.S. Appl. No. 13/400,652, filed Feb. 21, 2012.

International Search Report and Written Opinion mailed Jul. 10, 2014 for PCT/US2014/023655 claiming benefit of U.S. Appl. No. 13/800,369, filed Mar. 13, 2013.

European Communication Pursuant to Article 94(3) EPC mailed Nov. 24, 2014 for PCT/US2012/038351 which claims benefit of U.S. Appl. No. 13/111,007, filed May 19, 2011.

European Communication Pursuant to Article 94(3) EPC mailed Jan. 22, 2015 for PCT/US2007/013223 filed Jun. 5, 2007, which claims benefit of U.S. Appl. No. 60/812,694 filed Jun. 9, 2006 and U.S. Appl. No. 11/756,057 filed May 31, 2007.

European Communication Pursuant to Article 94(3) EPC mailed Feb. 4, 2015 for PCT/US2010/024584 filed Feb. 18, 2010, which claims benefit of U.S. Appl. No. 12/389,901 filed Feb. 20, 2009.

European Communication Pursuant to Article 94(3) EPC mailed Feb. 10, 2015 for PCT/US2009/039507 filed Apr. 3, 2009, which claims benefit of U.S. Appl. No. 12/103,824 filed Apr. 16, 2008.

International Preliminary Report on Patentability and Written Opinion mailed on Mar. 12, 2015 for PCT/US2013/057097 claiming benefit of U.S. Appl. No. 13/597,478, filed Aug. 29, 2012.

Japanese Office Action mailed on Apr. 7, 2015 for PCT/US2012/038351 filed May 17, 2012 claiming benefit of U.S. Appl. No. 13/111,007, filed May 19, 2011.

Patent Examiniation Report No. 1 mailed Feb. 16, 2015 for PCT/US2013/026875 filed Feb. 20, 2013, which claims benefit of U.S. Appl. No. 13/400,652, filed Feb. 21, 2012.

* cited by examiner

DRILL GUIDES FOR CONFIRMING ALIGNMENT OF PATIENT-SPECIFIC ALIGNMENT GUIDES

CROSS-REFERENCES TO RELATED APPLICATIONS

This application claims the benefit of U.S. provisional application No. 61/496,085, filed Jun. 13, 2011. The disclosure of the above application is incorporated herein by reference.

FIELD

The following relates to an orthopedic device and, more particularly, relates to an orthopedic device with a drill guide used for confirming alignment of a patient-specific alignment guide relative to a bone.

INTRODUCTION

The present teachings provide various drill guides for knee arthroplasty, including femoral and tibial guides. The drill guides are configured to reference corresponding patient-specific alignment guides and confirm the alignment of the patient-specific alignment guides relative to the mechanical axis of the knee joint before drilling holes into the bone through the patient-specific guides.

SUMMARY

An orthopedic device is disclosed. The orthopedic device includes a drill guide configured to be mounted on a patient-specific alignment guide for intraoperatively confirming alignment of the patient-specific alignment guide relative to a bone. The patient-specific alignment guide includes first and second referencing holes. The drill guide includes a main body with a first coupling member and a second coupling member. The first and second coupling members are configured to be received within the first and second referencing holes, respectively. The first and second coupling members each include corresponding first and second drill openings configured to align with the first and second referencing holes, respectively. The drill openings each guide a drilling tool toward the bone to drill corresponding holes in the bone. The main body also includes an alignment confirmation feature configured for confirming alignment of the patient-specific alignment guide relative to the bone before drilling holes in the bone.

An orthopedic method is also disclosed. The method includes intraoperatively nesting a three-dimensional patient-specific surface of a patient-specific alignment guide to a corresponding surface of the bone. The three-dimensional patient-specific surface is preoperatively configured to align the patient-specific alignment guide relative to the bone when nested to the corresponding surface in only one position. The patient-specific alignment guide includes a first referencing hole and a second referencing hole. The method also includes intraoperatively mounting a drill guide onto the patient-specific alignment guide by inserting first and second coupling members of the drill guide into the first and second referencing holes, respectively, and aligning corresponding drill openings of the first and second coupling members with the first and second referencing holes, respectively. Moreover, the method includes intraoperatively confirming that the patient-specific alignment guide is aligned relative to a mechanical axis of the bone using an alignment confirmation feature of the drill guide. Furthermore, the method includes drilling a hole into the bone through one of the drill openings after confirming that the patient-specific alignment guide is aligned relative to the mechanical axis of the bone.

Still further, an orthopedic device is disclosed. The orthopedic device includes a patient-specific alignment guide having a three-dimensional patient-specific surface that nests and closely conforms to a corresponding surface of a bone in only one position relative to the bone. The three-dimensional patient-specific surface is pre-operatively configured to align the alignment guide relative to a mechanical axis of the bone in only one position. The alignment guide includes a first referencing hole and a second referencing hole. Also, the orthopedic device includes a drill guide having a main body, a first projection, and a second projection. The first and second projections have first and second through holes, respectively, and the first and second projections are configured to be received within the first and second referencing holes, respectively, to intra-operatively couple the drill guide to the alignment guide and to guide a drilling tool toward the bone to form corresponding holes therein. The drill guide additionally includes an alignment opening configured to orient a rod along an axis parallel to the mechanical axis to confirm the alignment of the patient-specific alignment guide relative to the mechanical axis of the bone.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

The following description is merely exemplary in nature and is in no way intended to limit the present teachings, applications, or uses. For example, although the present teachings are discussed in association with resection guides and other instruments for performing knee surgery (e.g., knee arthroplasty), the present teachings can be used in association with other guides, templates, jigs, drills, rasps or other instruments used in various orthopedic procedures.

The present teachings are directed to various knee arthroplasty procedures that use patient-specific femoral or tibial alignment guides. The patient-specific alignment guides are configured preoperatively to register only in one position on the patient's bone and guide a drill template or drill guide to drill holes in the bone through referencing holes of the patient-specific alignment guide. The presents teachings further provide drill guides that can confirm intraoperatively the alignment and registration of the patient-specific guides relative to the mechanical axis of the bone.

Figure 2:
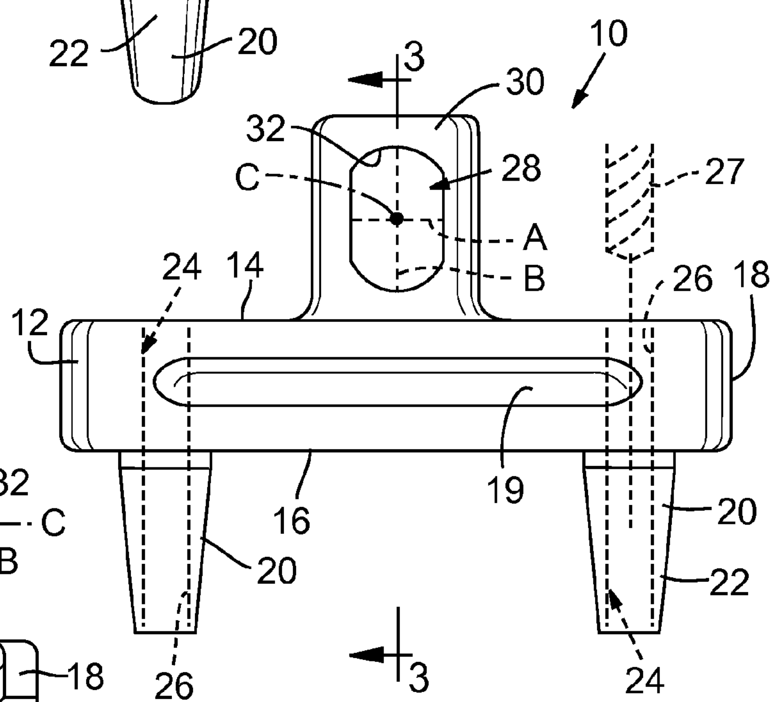
FIG. 2 is a front view of the drill guide of FIG. 1.
Figure 3:
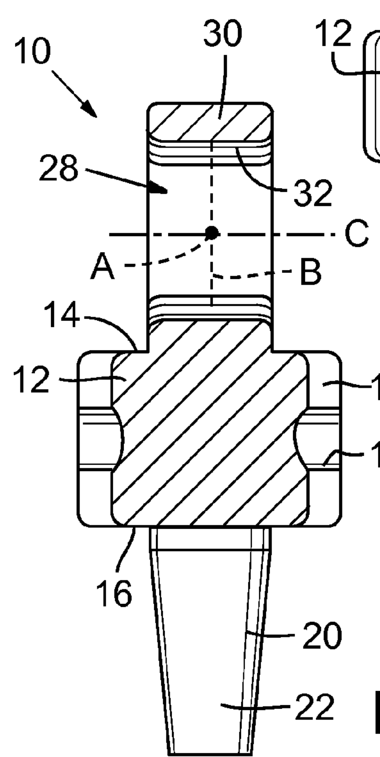
FIG. 3 is a section view of the drill guide taken along the line 3-3 of FIG. 2.
Figure 4:
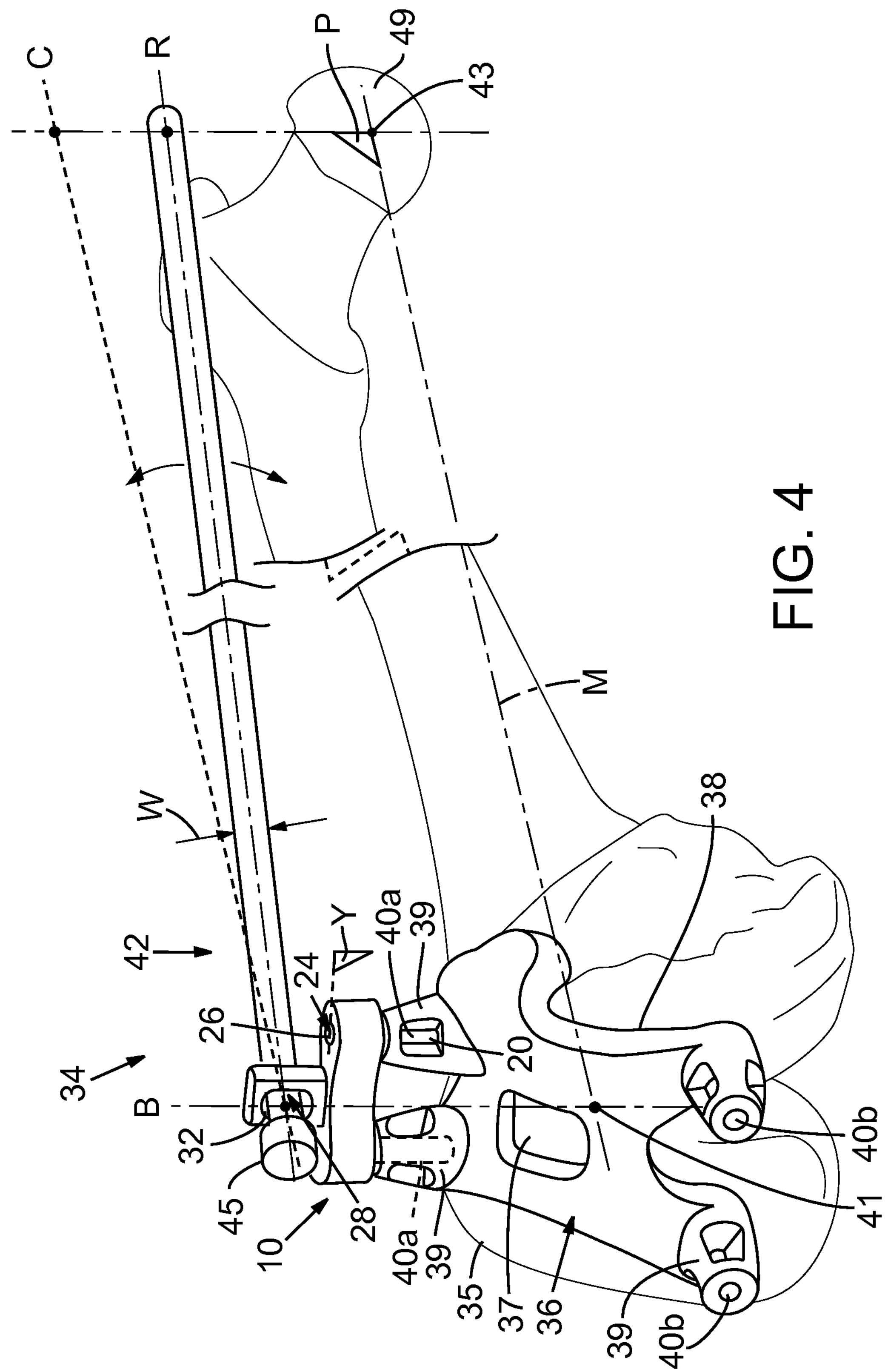
FIG. 4 is an isometric view of the drill guide of FIG. 1 shown operably coupled to a patient-specific alignment guide, which is nested on a femur.

Referring initially to FIGS. 1-4, an orthopedic device 34 for knee arthroplasty, such as implanting a prosthetic device (e.g., a knee joint prosthesis) in a patient's distal femur 35. The orthopedic device 34 can include a femoral drill guide 10 and a patient-specific alignment guide 36. As shown in FIG. 4, the drill guide 10 is configured to couple to the alignment guide 36 to intraoperatively confirm that the alignment guide 36 is properly aligned with respect to the femoral bone. Also, as will be discussed, the drill guide 10 can be used for guiding a drilling tool (e.g., a drill bit) during formation of one or more holes in the distal femur 35. The drill guide 10 is illustrated in detail in FIGS. 1-3.

Moreover, as will be discussed in relation to FIGS. 9 and 14, orthopedic devices 134, 234 can be configured for preparing a tibia 155, 255 for the orthopedic procedure as well. Various exemplary embodiments of tibial drill guide 110, 210 are illustrated in detail in FIGS. 6-8 and 11-13.

In each of these embodiments, the alignment of the patient-specific alignment guides 36, 136, 236 can be confirmed with the corresponding femoral or tibial drill guides 10, 110, 210. Alignment can be confirmed before any holes are drilled in the bone, and as such, the overall surgical procedure can be performed more quickly and efficiently.

Figure 1:
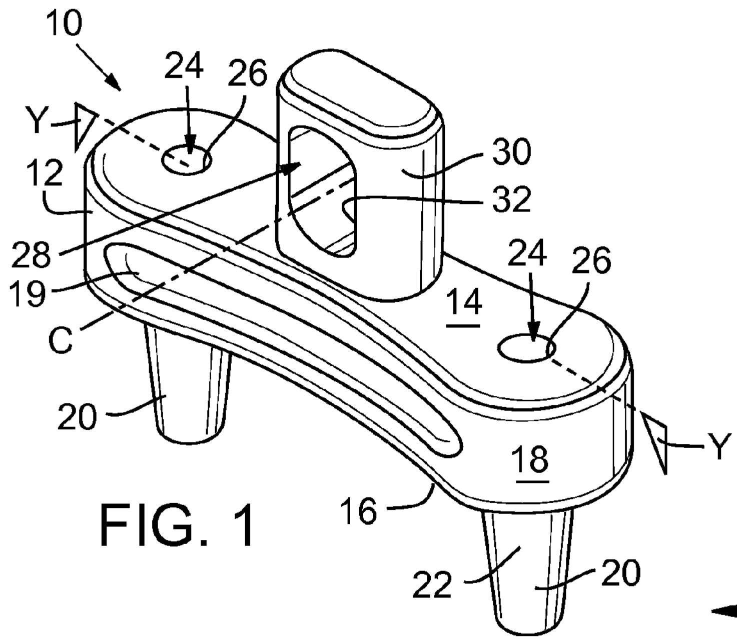
FIG. 1 is an isometric view of a drill guide according to various teachings of the present disclosure.

As shown in FIGS. 1-3, the femoral drill guide 10 can include a main body 12 with a top surface 14, a bottom surface 16, and a side surface 18. The top and bottom surfaces 14, 16 can be substantially flat, and the side surface 18 can be contoured. The side surface 18 can also include recessed slots 19 that improve handling of the drill guide 10.

The drill guide 10 can also include one or more coupling members 20. The coupling members 20 can be frusto-conically shaped projections that extend from the bottom surface 16. As such, the coupling members 20 can each include a tapered outer surface 22. The drill guide 10 can include any number of coupling members 20. For instance, in the embodiments illustrated, the drill guide 10 can include two coupling members 20 (i.e., first and second coupling members 20). The coupling members 20 can be spaced apart on opposite ends of the bottom surface 16.

Furthermore, as shown in FIGS. 1 and 2, the drill guide 10 can include one or more through-holes 24. The through-holes 24 can each extend continuously through the main body 12 and a respective one of the coupling members 20. A guide surface 26 can be defined by the inner diameter surface of each through-hole 24. Each guide surface 26 can have a circular cross section with a diameter that remains substantially constant along its length. The diameter of the guide surface 26 can also closely correspond to a drill bit 27 (shown in phantom in FIG. 2) or other drilling tool. Thus, the drill bit 27 can rotate and move axially through each through-hole 24, and the guide surface 26 can support the drill bit 27 such that the drill bit 27 remains aligned with the axis of the through-hole 24 as the drill bit 27 moves toward its target (e.g., a bone). Accordingly, the drill bit 27 can be supported and guided by the drill guide 10 for forming holes in the bone as will be discussed. Then, as will be discussed, referencing pins can be inserted and fixed within the holes. Subsequently, cutting guides, resection guides, or other tools can be attached to the bone via the referencing pins.

As shown in FIG. 1, a plane Y (i.e., a guide plane) can be defined by the longitudinal axes of the through-holes 24. Specifically, the longitudinal axes of both through-holes 24 can extend along the plane Y in the embodiments of FIG. 1.

The femoral drill guide 10 can additionally include an alignment confirmation feature 28. The alignment confirmation feature 28 can include a block 30 with an opening 32 (i.e., an alignment opening) formed therethrough. The block 30 can include a plurality of substantially flat sides, and the block 30 can extend from the top surface 14 of the main body 12. The opening 32 can be a through-hole that extends through the block 30. As shown in FIG. 2, the opening 32 can be elongated in cross-section so as to include a minor axis A and a major axis B that is longer than the minor axis A. The opening 32 can also include a longitudinal axis C (i.e., a confirmation axis) that is substantially straight and that extends substantially perpendicular to the plane Y as shown in FIG. 1.

Figure 5:
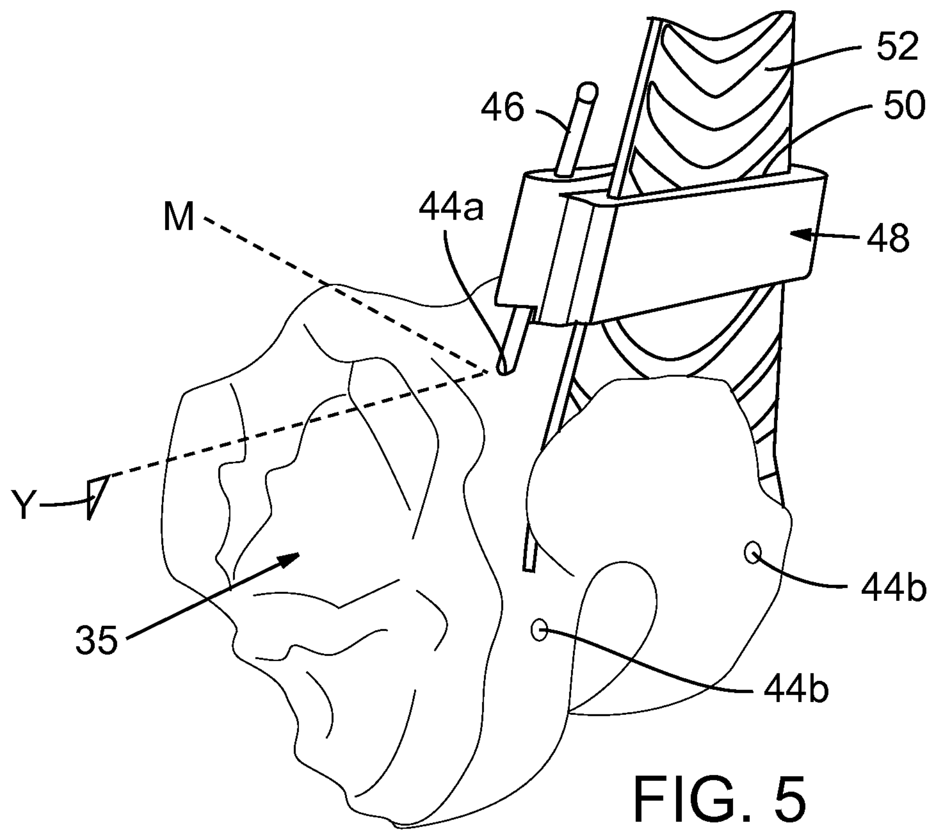
FIG. 5 is an isometric view of the femur of FIG. 4 during resection.

The alignment confirmation feature 28 can be used for confirming that the patient-specific alignment guide 36 (FIG. 4) is aligned as intended relative to the bone before any holes are drilled in the bone. Then, once proper alignment has been confirmed, holes can be drilled in the bone using the drill guide 10. Next, referencing pins 46, bone nails, or other similar bone fasteners can be positioned in the holes as shown in FIG. 5, and a resection guide 48 or other tools can be attached to those pins 46 to guide a resection tool 52, such as a reciprocating saw or cutting blade, after the patient-specific alignment guide 36 and the drill guide 10 are removed from the distal femur 35. Accordingly, the alignment confirmation feature 28 of the drill guide 10 can ultimately ensure that the referencing pins 46 and resection guide 48 will be aligned as intended relative to the bone.

It will be appreciated that the drill guide 10 can be a monolithic or unitary member made out of any suitable material. More specifically, the block 30 and the coupling members 20 can be integrally attached to the main body 12 to form a monolithic structure. The drill guide 10 can be made out of a metal (e.g., stainless steel), hard polymeric material, ceramic material, composite material, or any other material. Furthermore, the drill guide 10 can be formed in any suitable fashion (e.g., casting, milling, etc.). Additionally, it will be appreciated that the drill guide 10 can have various sizes and shapes, depending on the size of the patient's anatomy, etc. Moreover, the drill guide 10 can be designed and built preoperatively as will be discussed.

Referring now to FIGS. 4 & 5, the drill guide 10 is illustrated as part of the orthopedic device 34. The orthopedic device 34 can be used in preparation for implanting a knee joint prosthesis. Specifically, as shown in FIGS. 4 and 5, the device 34 can be used in preparation for resecting the distal femur 35; however, the device 34 can be used before resecting any other bone or before performing any other suitable surgical procedure.

For purposes of clarity, only the proximal and distal ends of the femoral bone are shown in FIG. 4, and the ends are translated toward each other along the mechanical axis M of the femoral bone. Moreover, it will be appreciated that other portions of the leg (e.g., muscle tissue, connective tissue, other bones, etc.) are not shown for clarity.

As mentioned above, the orthopedic device 34 can include a patient-specific alignment guide 36. Patient-specific alignment guides 36 and their method of manufacture are disclosed and described in detail in the commonly-owned, co-pending U.S. patent application Ser. No. 11/756057, filed on May 31, 2007, and published as U.S. Patent Publication No. 2007/0288030, which is hereby incorporated herein by reference in its entirety. The alignment guide 36 can be configured preoperatively to include a three-dimensional patient-specific surface 38 that nests and closely conforms to a corresponding surface 37 of the distal femur 35 in only one position. For instance, the patient-specific surface 38 can be shaped and contoured to nest and closely conform to a portion of anterior and distal (i.e., condylar) surfaces 37 of the distal femur 35 as shown in FIG. 4. Specifically, a three dimensional electronic model of the patient's knee joint or other anatomy can be generated from Magnetic Resonance Imaging (MRI) or other imaging data of the patient's anatomy, and the patient-specific alignment guide 36 can be designed such that the patient-specific surface 38 can be complementary to and nestingly mate with a corresponding surface of the distal femur 35 with or without articular cartilage. The drill guide 10 (discussed above) can also be designed preoperatively to be operably coupled to the alignment guide 36 as will be discussed. This preoperative design process can be performed, for instance, using software that is commercially available from Materialise USA of Plymouth, Mich.

The alignment guide 36 can also include one or more frusto-conic projections 39, each with a referencing hole 40*a*, 40*b* extending therethrough. The alignment guide 36 can include any number of referencing holes 40*a*, 40*b*, and the holes 40*a*, 40*b* can be in any position/orientation relative to the distal femur 35. In the embodiments illustrated, for instance, the alignment guide 36 includes two anterior holes 40*a* and two distal holes 40*b*. When the alignment guide 36 is nested on the distal femur 35, the anterior holes 40*a* are directed generally toward the anterior surface of the distal femur 35, and the distal holes 40*b* are directed generally toward the distal surface of the distal femur 35. The alignment guide 36 can also be designed such that the holes 40*a*, 40*b* have a predetermined orientation relative to the bone. For instance, when nested against the distal femur 35, the anterior holes 40*a* can both be substantially perpendicular to a mechanical axis M of the femoral bone. The mechanical axis M is defined between a centerpoint 43 of the femoral head 49 and a central point 41 between the condylar surfaces of the distal femur 35.

As shown in FIG. 4, the drill guide 10 can operably couple to the alignment guide 36. Specifically, the coupling members 20 can be simultaneously received within the anterior holes 40*a*. The anterior holes 40*a* can have a female-tapered shape so as to nest with the tapered outer surfaces 22 of the coupling members 20. When coupled as such, the through holes 24 of the drill guide 10 can substantially align with the holes 40*a*, respectively. Also, when the drill guide 10 is mounted to the alignment guide 36, the confirmation axis C can be substantially parallel to a mechanical axis M of the femoral bone, assuming that the alignment guide 36 is aligned as intended relative to the mechanical axis M.

The device 34 can additionally include an alignment rod 42. The rod 42 can be rigid and elongate with a substantially straight axis R. The rod 42 can have a substantially circular cross section, or the rod 42 can have a different cross sectional shape. Also, the rod 42 can have a width W (i.e., diameter) that allows the rod 42 to be received (e.g., slidingly received) within the opening 32 of the drill guide 10. For instance, the width W can be substantially equal or slightly less than the minor axis A of the opening 32 (FIG. 2). However, the width W can be significantly less than the major axis B of the opening 32. The rod 42 can also include an enlarged head 45 that limits sliding movement of the rod 42 relative to the drill guide 10.

The rod 42 can be slidingly received within the opening 32 of the drill guide 10 to thereby confirm that the alignment guide 36 is, in fact, properly aligned relative to the femoral bone (i.e., in a target orientation). The target orientation can be any suitable orientation relative to the femoral bone (e.g., relative to the mechanical axis M). For instance, the target orientation can be such that the plane Y is substantially perpendicular to the mechanical axis M. If the alignment guide 36 is at this target orientation, then the axis C should be substantially parallel to the mechanical axis M. Thus, by sliding the rod 42 along the axis C, the rod axis R should likewise be parallel to the mechanical axis M. Otherwise, the rod 42 can be rotated about the axis A (FIGS. 2 and 3) of the drill guide 10 (e.g., to avoid interference with anatomical soft tissue) and the rod axis R can remain within a plane P defined by the mechanical axis M and the confirmation axis C as shown in FIG. 4. If these conditions are satisfied, then it is confirmed that the alignment guide 36 is properly aligned. Otherwise, the alignment guide 36 is misaligned.

It will be appreciated that the predetermined alignment or target orientation of the alignment guide 36 could be relative to any other anatomical feature or anatomic axis other than the mechanical axis M. Also, it will be appreciated that the predetermined alignment or target orientation could be disposed at a predetermined offset angle relative to the mechanical axis M.

Thus, during the surgical procedure, the patient-specific alignment guide 36 can be nested against the corresponding surface 37 of the distal femur 35. Then, the coupling members 20 of the drill guide 10 can be removably inserted into the corresponding pair of referencing holes 40*a* of the guide 36 as shown in FIG. 4. Next, the rod 42 can be slidingly inserted into the opening 32 in the drill guide 10, and the orientation of the rod axis R can be inspected relative to the mechanical axis M and the plane P. Specifically, it can be determined if the rod axis R lies substantially within the plane P. If so, it is confirmed that the alignment guide 36 is properly aligned. If not, misalignment of the guide 36 can be recognized. Advantageously, this procedure can be performed before any holes are drilled or any resections are made on the distal femur 35.

Once proper alignment of the guide 36 has been confirmed, the rod 42 can be withdrawn. Then, the drill bit 27 (FIG. 2) can be introduced into each of the holes 24 of the drill guide 10, and anterior drill holes 44*a* (FIG. 5) can be formed in the distal femur 35 while being guided by the guide surfaces 26 of the drill guide 10. Specifically, holes 44*a* in the distal, anterior portion of the distal femur 35 can be formed first. Distal holes 44*b* for a cutting block can be formed through the referencing holes 40*b* of the alignment guide, as shown in FIG. 5.

Next, referencing pins 46 can be driven into respective ones of the drill holes 44*a* on the anterior surface of the distal femur 35 as shown in FIG. 5. Subsequently, a known distal resection guide 48 with a guide surface 50 can be attached to the distal femur 35 by sliding the guide 48 onto both pins 46. As shown in FIG. 5, the pins 46 are disposed on the plane Y, which was previously confirmed to be perpendicular to the mechanical axis M of the femoral bone. Thus, when a resection tool 52 (e.g., a reciprocating blade) is guided toward the distal femur 35 by the guide surface 50, the resection can be substantially perpendicular to the mechanical axis M, as desired.

Figure 6:
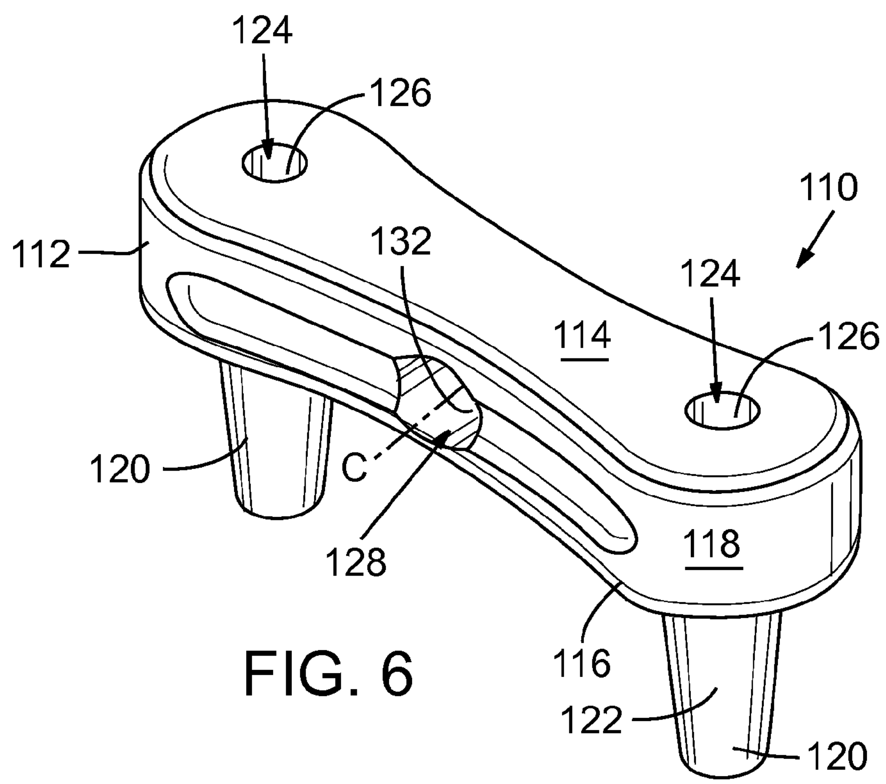
FIG. 6 is an isometric view of a drill guide according to additional teachings of the present disclosure.
Figure 7:
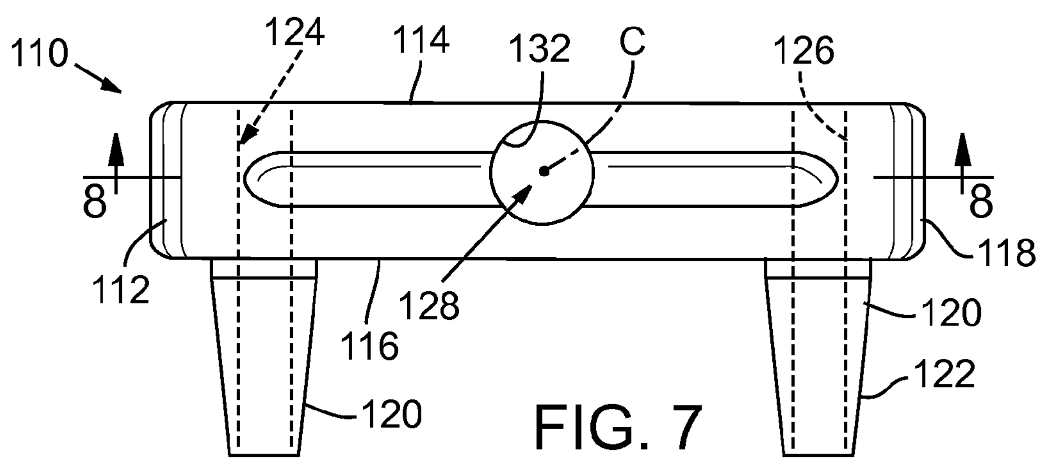
FIG. 7 is a front view of the drill guide of FIG. 6.
Figure 8:
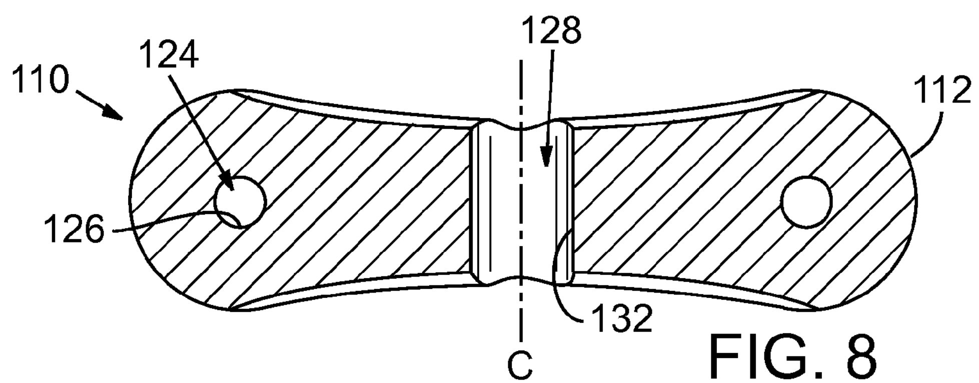
FIG. 8 is a section view of the drill guide taken along the line 8-8 of FIG. 7.

Referring now to FIGS. 6-8, exemplary embodiments of a tibial drill guide 110 are illustrated. Components that correspond to those of the embodiments of FIGS. 1-4 are indicated with corresponding reference numbers increased by 100.

Figure 9:
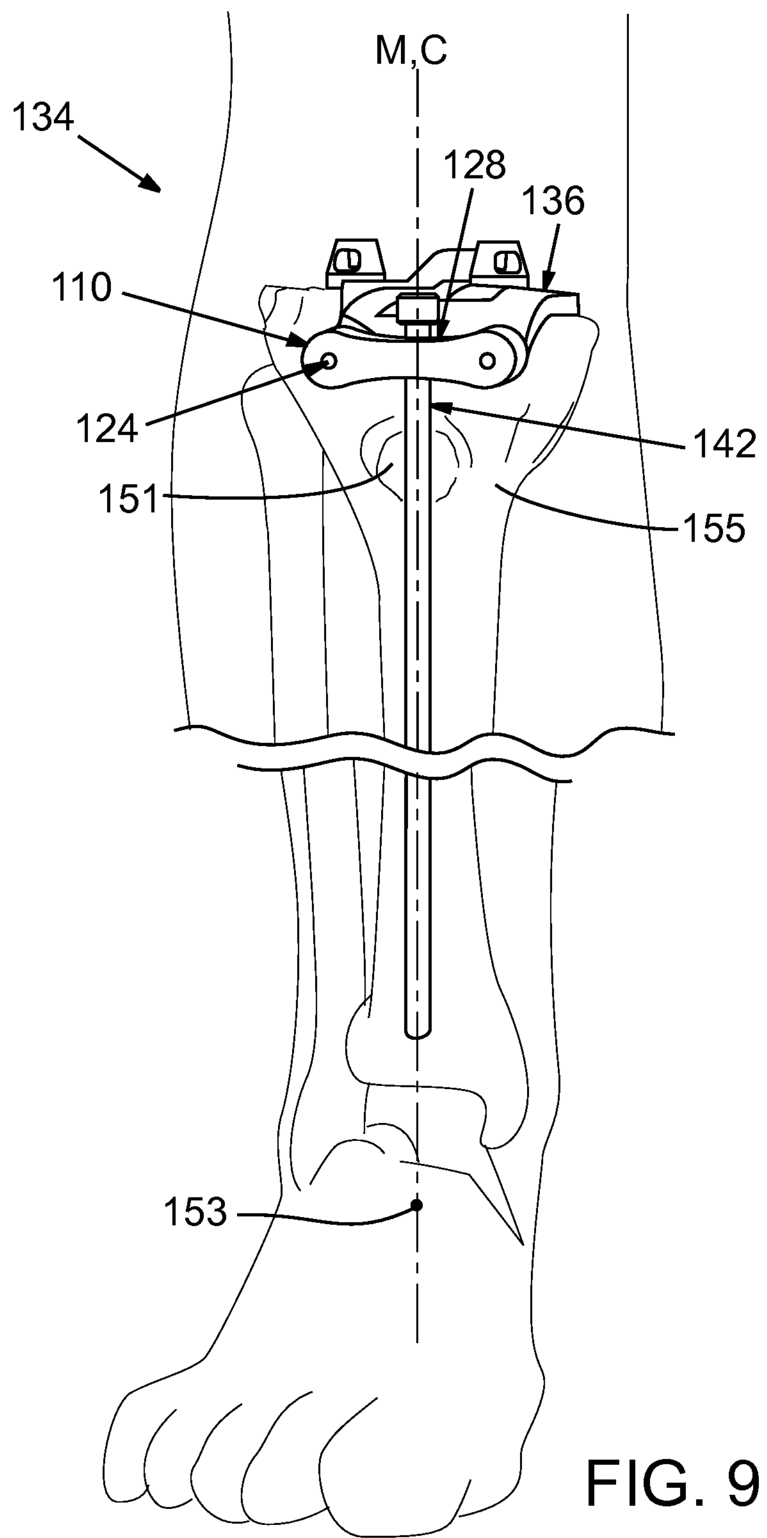
FIG. 9 is an isometric view of the drill guide of FIG. 6 shown operably coupled to a patient specific alignment guide, which is nested on a tibia.
Figure 11:
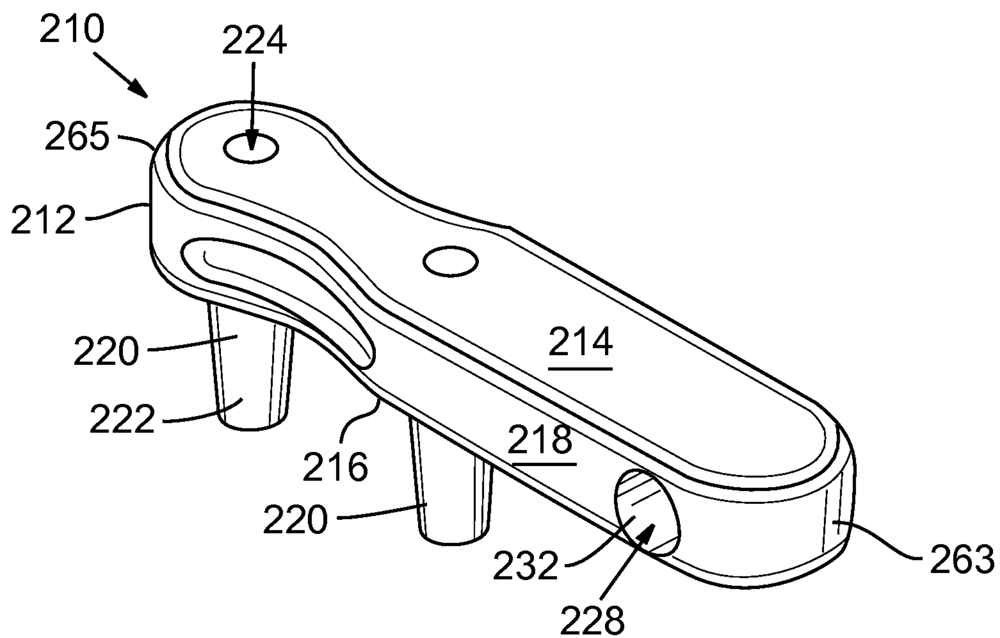
FIG. 11 is an isometric view of a drill guide according to additional teachings of the present disclosure.
Figure 12:
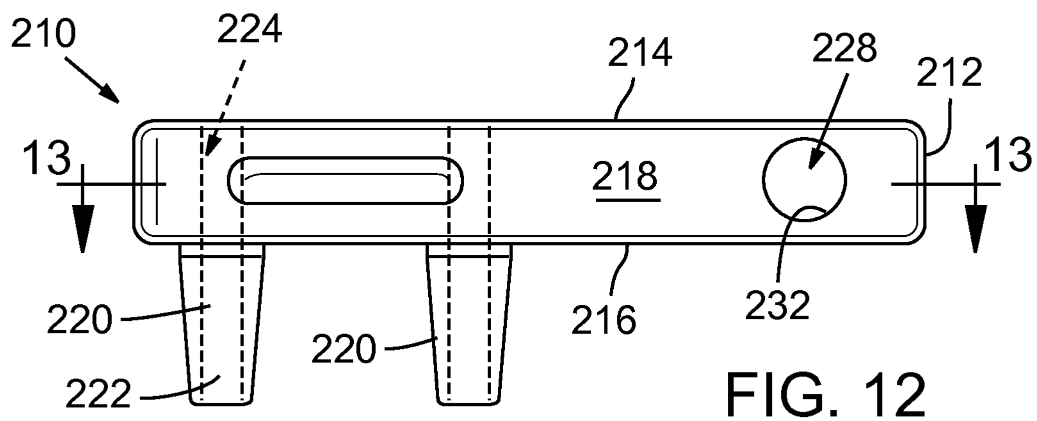
FIG. 12 is a front view of the drill guide of FIG. 11.
Figure 13:
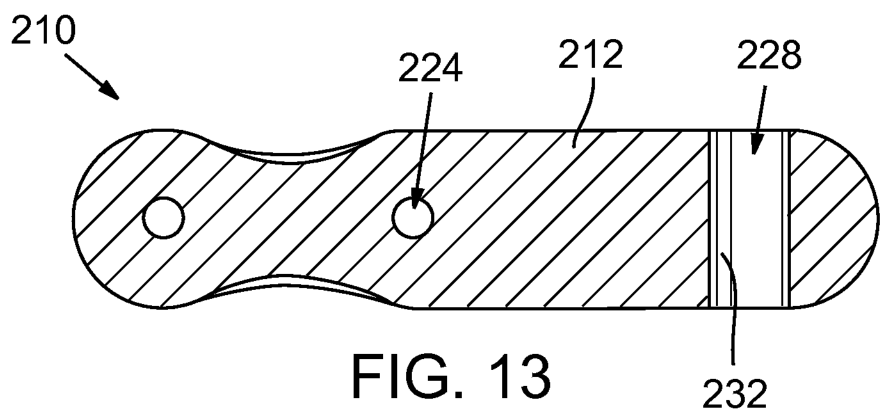
FIG. 13 is a section view of the drill guide taken along the line 13-13 of FIG. 12.

As will be discussed, the tibial drill guide 110 can be used in connection with resecting a tibia 155 (FIG. 9). However, the drill guide 110 can be used for resecting another bone without departing from the scope of the present disclosure.

As shown, the opening 132 can extend directly through the main body 112 of the drill guide 110. The opening 132 can also be substantially centered between the coupling members 120 such that the axis C of the opening 132 defines a line of symmetry of the main body 112.

Furthermore, the opening 132 can have a cross section that closely conforms to that of the alignment rod 142 (FIG. 9). As such, the rod 142 can only slide in a direction substantially parallel to the axis C of the opening 132.

Thus, as shown in FIG. 9, the drill guide 110 can be used during resection of the tibia 155 to confirm that the alignment guide 136 is aligned relative to the mechanical axis M of the tibia 155. The mechanical axis M of the tibia 155 is defined by the tibial tubercle 151 and a center point of the ankle 153.

Figure 10:
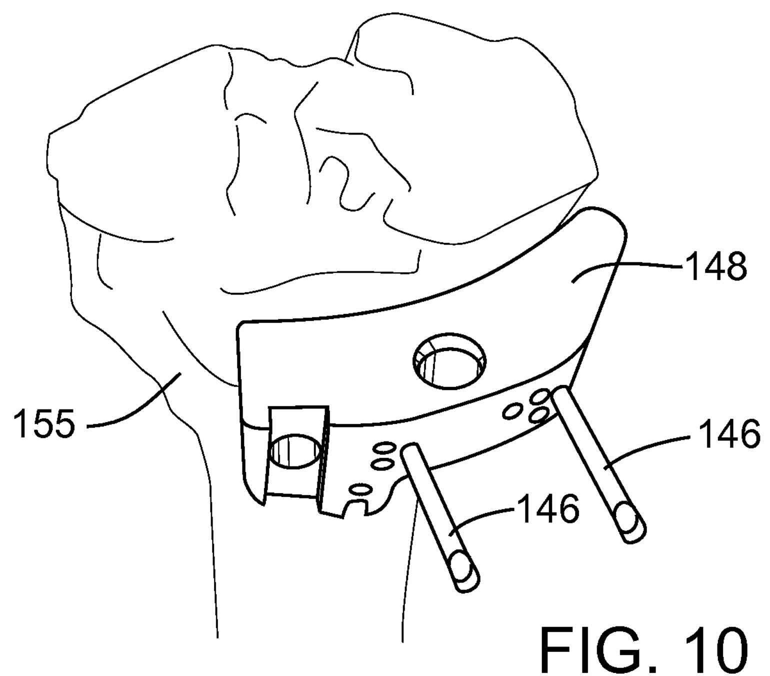
FIG. 10 is an isometric view of the tibia of FIG. 9 shown with a resection guide mounted thereon.

Once alignment of the alignment guide 136 has been confirmed as shown in FIG. 9, the drill guide 110 can be used to guide the drilling of holes for pins 146 (FIG. 10). Subsequently, the tibial resection guide 148 can be attached to the tibia 155 via the pins 146 as shown in FIG. 10, and the tibia 155 can be resected in a known manner.

Figure 14:
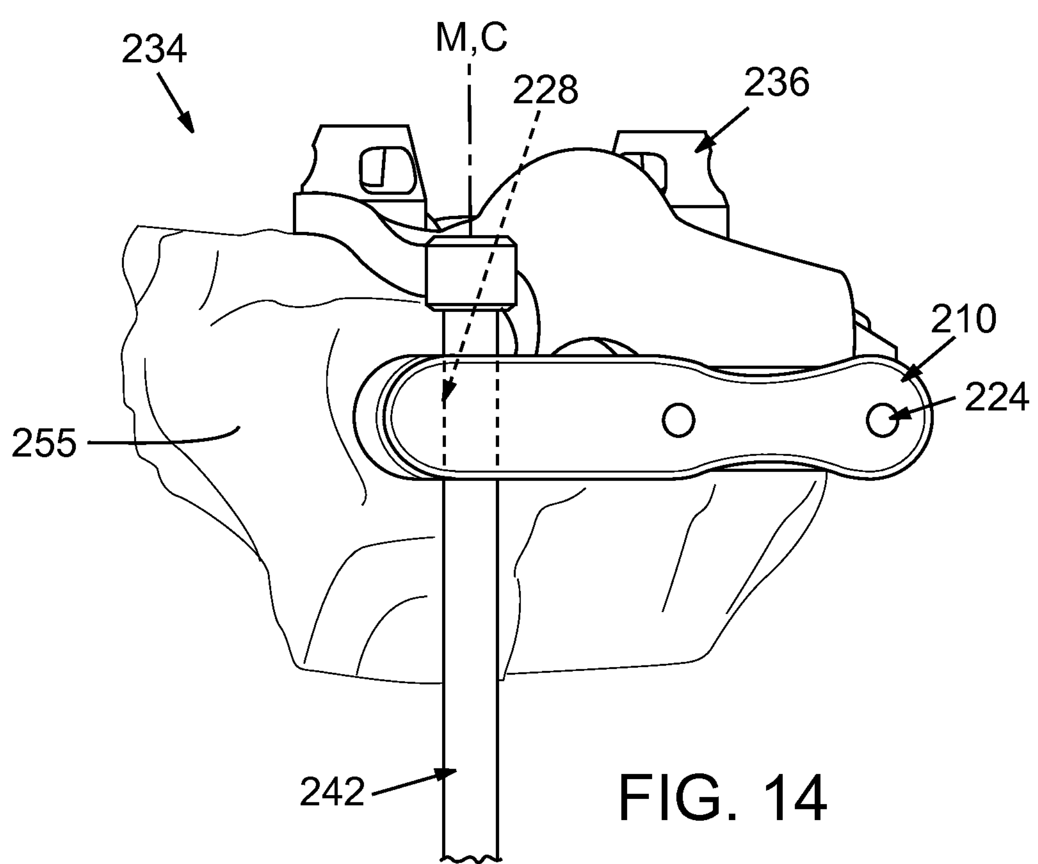
FIG. 14 is an isometric view of the drill guide of FIG. 11 shown operably coupled to a patient specific alignment guide, which is nested on a tibia.

Referring now to FIGS. 11-14, additional exemplary embodiments of the drill guide 210 are illustrated. Components that correspond to those of the embodiments of FIGS. 6-8 are indicated with corresponding reference numbers increased by 100. Like the embodiments of FIGS. 6-8, the drill guide 210 can be used in connection with resecting a tibia 255 (FIG. 14). However, the drill guide 210 can be used for resecting another bone without departing from the scope of the present disclosure.

As shown, the opening 232 can extend directly through the main body 212 of the drill guide 110. However, the opening 232 can be off-center such that the opening 232 is disposed adjacent a first end 263 and is spaced away from a second end 265 of the main body 212. Furthermore, the opening 232 can be disposed on one side of the main body 112 relative to the coupling members 220.

Thus, as shown in FIG. 14, the drill guide 210 can be used during resection of the tibia 255 to confirm that the alignment guide 236 is properly oriented relative to the mechanical axis M of the tibia 255. Once alignment of the drill guide 210 has been confirmed as shown in FIG. 14, holes can be drilled using the drill guide 210 and the subsequent resection of the tibia 255 can be performed as discussed above with respect to FIG. 10.

Accordingly, the drill guide 210 allows the surgeon to quickly and efficiently check that the alignment guide 236 is properly aligned relative to the patient's anatomy. This check can be performed before the bone is drilled and/or resection cuts are made.

In summary, the orthopedic device 34, 134, 234 of the present teachings provide an intraoperative confirmation of the alignment of patient-specific alignment guides relative to corresponding mechanical axes of the bone prior to drilling or resection of the bone during an arthroplasty. The drill guide 10, 110, 210 is configured to intraoperatively couple to the patient-specific alignment guide 36, 136, 236, and the alignment rod 42, 142, 242 can be coupled to the drill guide 10, 110, 210 to confirm that the alignment guide 36, 136, 236 is aligned as intended relative to the bone. This confirmation step can be performed before any of the drill holes are formed in the bone. Thus, any unintended misalignment can be corrected early in the procedure. Accordingly, the procedure can be performed accurately and efficiently.

It will be appreciated that the drill guide 10, 110, 210 can vary in a number of ways without departing from the scope of the present disclosure. For instance, the alignment confirmation feature 28, 128, 228 of the drill guide 10, 110, 210 can be another feature other than an opening 32, 132, 232 that receives the rod 42, 142, 242. For instance, the alignment confirmation feature 28, 128, 228 could be a male connector, and the rod 42, 142, 242 could include a female opening that receives the male connector to thereby attach the rod 42, 142, 242 to the drill guide 10, 110, 210. It will also be appreciated that the rod 42, 142, 242 could be replaced by a laser pointer that is coupled to the alignment confirmation feature 28, 128, 228 of the drill guide 10, 110, 210 to confirm that the alignment guide 36, 136, 236 is properly aligned.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic device comprising:

a drill guide configured to be mounted on a patient-specific alignment guide for intraoperatively confirming alignment of the patient-specific alignment guide relative to a bone, the patient-specific alignment guide including a first referencing hole and a second referencing hole, the drill guide including:

a main body with a first coupling member and a second coupling member, the first and second coupling members configured to be received within the first and second referencing holes, respectively, the first and second coupling members including corresponding first and second drill openings configured to align with the first and second referencing holes, respectively, for guiding a drilling tool toward the bone to drill corresponding holes in the bone, the main body further including an alignment confirmation feature configured for confirming alignment of the patient-specific alignment guide relative to the bone before drilling holes in the bone, wherein the alignment confirmation feature includes an alignment opening configured to receive a rod, and the alignment opening is configured to allow the rod to at least axially slide and pivot within the alignment opening.

2. The orthopedic device of claim 1, wherein the alignment confirmation feature is configured for confirming that the patient-specific alignment guide is aligned relative to a mechanical axis of the bone.

3. The orthopedic device of claim 2, wherein the alignment confirmation feature orients a longitudinal rod axis of the rod parallel to the mechanical axis to thereby confirm alignment of the patient-specific alignment guide.

4. The orthopedic device of claim 3, wherein the alignment opening is elongate in cross-section, the alignment opening having a minor axis that substantially corresponds to a cross-sectional width of the rod, the alignment opening having a major axis that is greater than the cross-sectional width of the rod.

5. The orthopedic device of claim 3, further comprising a block that extends away from a surface of the main body, the alignment opening extending through the block.

6. The orthopedic device of claim 3, wherein the alignment opening passes directly through the main body.

7. The orthopedic device of claim 3, wherein the alignment opening defines a line of symmetry of the main body.

8. The orthopedic device of claim 3, wherein the alignment opening is disposed adjacent a first end of the main body and is spaced away from a second end of the main body.

9. The orthopedic device of claim 1, further comprising a patient-specific alignment guide, the patient-specific alignment guide having a three-dimensional patient-specific surface preoperatively configured to nest and closely conform to a corresponding surface of the bone in only one position relative to the bone.

10. The orthopedic device of claim 1, wherein the main body includes a plurality of drill openings, each having a respective longitudinal axis, the longitudinal axes of the drill openings cooperating to define a guide plane, and wherein the alignment confirmation feature defines a confirmation axis that is substantially perpendicular to the guide plane.

11. The orthopedic device of claim 1, wherein at least one of the first and second coupling members has a tapered outer surface that is removably received within the corresponding one of the first and second referencing holes.

12. The orthopedic device of claim 1, wherein the bone is at least one of a tibia and a femur.

13. An orthopedic device comprising:

a patient-specific alignment guide having a three-dimensional patient-specific surface that nests and closely conforms to a corresponding surface of a bone in only one position relative to the bone, the three-dimensional patient-specific surface being pre-operatively configured to align the alignment guide relative to a mechanical axis of the bone in only one position, the alignment guide including a first referencing hole and a second referencing hole;

a drill guide including a main body, a first projection, and a second projection, the first and second projections having first and second through holes, respectively, the first and second projections configured to be received within the first and second referencing holes, respectively, to intra-operatively couple the drill guide to the alignment guide and to guide a drilling tool toward the bone to form corresponding holes therein, the drill guide additionally including an alignment opening configured to orient a rod along an axis parallel to the mechanical axis to confirm the alignment of the patient-specific alignment guide relative to the mechanical axis of the bone, wherein the alignment opening is configured to allow the rod to at least axially slide and pivot within the alignment opening.

14. The orthopedic device of claim 1, wherein the first and second projections each include a tapered outer surface.

15. The orthopedic device of claim 1, wherein the alignment opening is elongate in cross section, the alignment opening having a minor axis that substantially corresponds to a width of the rod, the alignment opening having a major axis that is greater than the width of the rod.

16. The orthopedic device of claim 1, wherein the drill guide is a femoral drill guide for drilling holes in a femur, wherein the alignment opening is elongate in cross section, the alignment opening having a minor axis that substantially corresponds to a cross-sectional width of the rod, the alignment opening having a major axis that is greater than the cross-sectional width of the rod, the alignment opening passing through a block that extends away from a surface of the main body.

17. The orthopedic device of claim 1, wherein the drill guide is a tibial drill guide for drilling holes in a tibia, wherein the alignment opening passes directly through the main body, the alignment opening defining a line of symmetry of the main body.

18. The orthopedic device of claim 1, wherein the drill guide is a tibial drill guide for drilling holes in a tibia, wherein the alignment opening passes directly through the main body, the alignment opening being disposed adjacent a first end of the main body and being spaced away from a second end of the main body.

19. An orthopedic device comprising:

a patient-specific alignment guide having a three-dimensional patient-specific surface that nests and closely conforms to a corresponding surface of a bone in only one position relative to the bone, the three-dimensional patient-specific surface being pre-operatively configured to align the alignment guide relative to a mechanical axis of the bone in only one position, the alignment guide including a first referencing hole and a second referencing hole;

a drill guide including a main body, a first projection, and a second projection, the first and second projections configured to be received within the first and second referencing holes, respectively, to intra-operatively couple the drill guide to the alignment guide and to guide a drilling tool toward the bone to form a corresponding hole therein, the drill guide additionally including at least one drill opening and an alignment opening configured to orient a rod along an axis parallel to the mechanical axis to confirm the alignment of the patient-specific alignment guide relative to the mechanical axis of the bone, wherein the alignment opening is configured to allow the rod to at least axially slide and pivot within the alignment opening.

20. The orthopedic device of claim 19, wherein the alignment opening is elongate in cross section, the alignment opening having a minor axis that substantially corresponds to a width of the rod, the alignment opening having a major axis that is greater than the width of the rod.

21. The orthopedic device of claim 19, further comprising a block that extends away from a surface of the main body, the alignment opening extending through the block.

22. The orthopedic device of claim 21, wherein the at least one drill opening includes a first drill opening extending through the first projection and a second drill opening extending through the second projection.

* * * * *

UNITED STATES PATENT AND TRADEMARK OFFICE

CERTIFICATE OF CORRECTION

PATENT NO. : 9,084,618 B2
APPLICATION NO. : 13/493509
DATED : July 21, 2015
INVENTOR(S) : Serbousek et al.

It is certified that error appears in the above-identified patent and that said Letters Patent is hereby corrected as shown below:

Claims

In column 9, line 62, in Claim 14, delete "claim 1," and insert --claim 13,--, therefor In column 10, line 1, in Claim 15, delete "claim 1," and insert --claim 13,--, therefor In column 10, line 6, in Claim 16, delete "claim 1," and insert --claim 13,--, therefor In column 10, line 15, in Claim 17, delete "claim 1," and insert --claim 13,--, therefor In column 10, line 20, in Claim 18, delete "claim 1," and insert --claim 13,--, therefor Signed and Sealed this
Twenty-second Day of December, 2015

Michelle K. Lee

Michelle K. Lee
*Director of the United States Patent and Trademark Office*